United States Patent
Choi et al.

(10) Patent No.: US 11,711,974 B2
(45) Date of Patent: Jul. 25, 2023

(54) COMPOUND AND PHOTOELECTRIC DEVICE, IMAGE SENSOR AND ELECTRONIC DEVICE INCLUDING THE SAME

(71) Applicant: Samsung Electronics Co., Ltd., Suwon-si (KR)

(72) Inventors: Taejin Choi, Suwon-si (KR); Chul Baik, Suwon-si (KR); Ji Soo Shin, Suwon-si (KR); Sung Young Yun, Suwon-si (KR); Kyung Bae Park, Hwaseong-si (KR); Gae Hwang Lee, Seongnam-si (KR); Yeong Suk Choi, Suwon-si (KR); Chui Joon Heo, Busan (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 374 days.

(21) Appl. No.: 16/853,022

(22) Filed: Apr. 20, 2020

(65) Prior Publication Data

US 2020/0350500 A1     Nov. 5, 2020

(30) Foreign Application Priority Data

May 2, 2019   (KR) ................. 10-2019-0051852

(51) Int. Cl.
| | |
|---|---|
| H01L 27/146 | (2006.01) |
| C07D 209/00 | (2006.01) |
| C07D 421/04 | (2006.01) |
| C07D 421/14 | (2006.01) |
| H10K 85/60 | (2023.01) |
| H10K 19/20 | (2023.01) |
| H10K 30/30 | (2023.01) |
| H10K 39/32 | (2023.01) |

(52) U.S. Cl.
CPC ......... H10K 85/654 (2023.02); C07D 209/00 (2013.01); C07D 421/04 (2013.01); C07D 421/14 (2013.01); H10K 19/20 (2023.02); H10K 30/30 (2023.02); H10K 39/32 (2023.02); H10K 85/60 (2023.02); H10K 85/657 (2023.02); *H01L 27/14647* (2013.01)

(58) Field of Classification Search
CPC ............ H01L 27/146; H01L 27/14645; H01L 27/14647; H01L 27/14621; H01L 27/14667; Y02E 10/549; C07D 209/00; C07D 421/04; C07D 421/14
See application file for complete search history.

(56) References Cited

U.S. PATENT DOCUMENTS

| | | |
|---|---|---|
| 8,525,577 B2 | 9/2013 | Yofu et al. |
| 9,786,847 B2 | 10/2017 | Lim et al. |
| 9,818,956 B2 | 11/2017 | Ro et al. |
| 9,941,477 B2 | 4/2018 | Choi et al. |
| 10,224,486 B2 | 3/2019 | Yagi et al. |
| 10,236,449 B2 | 3/2019 | Yun et al. |
| 10,326,083 B2 | 6/2019 | Yagi et al. |
| 10,461,256 B2 | 6/2019 | Yagi et al. |
| 10,566,544 B2 | 2/2020 | Shibuya et al. |

FOREIGN PATENT DOCUMENTS

| | | |
|---|---|---|
| JP | 2005123033 A | 5/2005 |
| KR | 101324781 B1 | 11/2013 |
| KR | 20160046567 A | 4/2016 |
| KR | 20160052448 A | 5/2016 |
| KR | 20160062527 A | 6/2016 |
| KR | 20170037390 A | 4/2017 |
| KR | 20170060488 A | 6/2017 |
| KR | 20170114839 A | 10/2017 |
| KR | 20170126753 A | 11/2017 |
| KR | 20170137648 A | 12/2017 |

OTHER PUBLICATIONS

RN2514599-29-0, registry database compound, 2020.*
H. Seo et al., 'Color Sensors with Three Vertically Stacked Organic Photodetectors' *Japanese Journal of Applied Physics*, vol. 46, No. 49, Sep. 2007, pp. L1240-L1242.
S. Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.
M. Ihama et al., 'CMOS Image Sensor with a Thin Overlaid Panchromatic Organic Photoconductive Layer for Sensors with Reduced Pixel Size' *IDW* 2009, pp. 2123-2126.
Seon-Jeong LIM et al., "Organic-on-silicon complementary metal-oxide-semiconductor colour image sensors" Scientific Reports, published Jan. 12, 2015.
Juha Alakarhu, 'Image Sensors and Image Quality in Mobile Phones' *International Image Sensor Workshop*, Jun. 2007.

* cited by examiner

*Primary Examiner* — Sun Jae Yoo
(74) *Attorney, Agent, or Firm* — Harness, Dickey & Pierce, P.L.C.

(57) ABSTRACT

A compound of Chemical Formula 1, and an organic photoelectric device, an image sensor, and an electronic device including the same are disclosed:

[Chemical Formula 1]

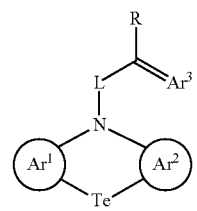

In Chemical Formula 1, each substituent is the same as defined in the detailed description.

22 Claims, 9 Drawing Sheets

COMPOUND AND PHOTOELECTRIC DEVICE, IMAGE SENSOR AND ELECTRONIC DEVICE INCLUDING THE SAME

CROSS-REFERENCE TO RELATED APPLICATION

This application claims priority to and the benefit of Korean Patent Application No. 10-2019-0051852 filed in the Korean Intellectual Property Office on May 2, 2019, the entire contents of which are incorporated herein by reference.

BACKGROUND

1. Field

Example embodiments provide a compound and a photoelectric device, an image sensor, and an electronic device including the same.

2. Description of the Related Art

A photoelectric device converts light into an electrical signal using photoelectric effects. The photoelectric device may include a photodiode, a phototransistor, and the like, and it may be applied to an image sensor, an organic light emitting diode, and the like.

An image sensor including a photodiode requires high resolution and thus a small pixel. At present, a silicon photodiode is widely used, but it has a problem of deteriorated sensitivity since silicon photodiode has a smaller absorption area due to small pixels. Accordingly, an organic material that is capable of replacing silicon has been researched.

The organic material has a high extinction coefficient and selectively absorbs light in a particular wavelength region depending on a molecular structure, and thus may simultaneously replace a photodiode and a color filter and resultantly improve sensitivity and contribute to high integration.

SUMMARY

Example embodiments provide a compound capable of selectively absorbing light in a green wavelength region and having improved thermal stability.

Example embodiments also provide a photoelectric device (e.g., organic photoelectric device) capable of selectively absorbing light in the green wavelength region and maintaining good efficiency even under high temperature conditions.

Example embodiments also provide an image sensor including the photoelectric device (e.g., organic photoelectric device).

Example embodiments also provide an electronic device including the image sensor.

According to example embodiments, a compound is represented by Chemical Formula 1.

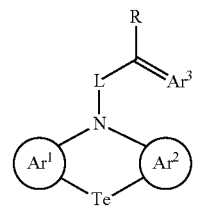

[Chemical Formula 1]

In Chemical Formula 1,
Ar$^3$ is a substituted or unsubstituted C6 to C30 hydrocarbon cyclic group having two functional groups including one of C=O, C=S, C=Se, or C=Te, a substituted or unsubstituted C6 to C30 heterocyclic group having a functional group of C=O, C=S, C=Se, or C=Te, or a fused ring thereof, R is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, Ar$^1$ and Ar$^2$ are the same or different and are each independently a substituted or unsubstituted C6 to C30 arene group, a substituted or unsubstituted C3 to C30 heteroarene group, or a condensed ring thereof, and L is a linker represented by Chemical Formula A or Chemical Formula B:

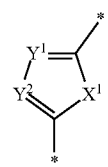

[Chemical Formula A]

wherein, in Chemical Formula A,
X$^1$ is —Se—, —Te—, —O—, —S(=O)—, —S(=O)$_2$—, —NR$^a$—, —SiR$^b$R$^c$—, or —GeR$^d$R$^e$—,
Y$^1$ and Y$^2$ are the same or different and are each independently CR$^f$ or N,
when Y$^1$ and Y$^2$ are CR$^y$, Y$^1$ and Y$^2$ are each independently present or are linked with each other to provide a ring,
R$^a$ to R$^f$ are the same or different and are each independently hydrogen, deuterium, or a substituted or unsubstituted C1 to C10 alkyl group, and
* is a linking point,

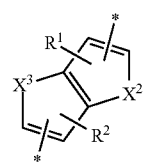

[Chemical Formula B]

wherein in Chemical Formula B,
X$^2$ and X$^3$ are the same or different and are each independently —S—, —Se—, —Te—, —O—, —S(=O)—, —S(=O)$_2$—, —NR$^a$—, —SiR$^b$R$^c$—, or —GeR$^d$R$^e$—,
R$^a$ to R$^e$ are the same or different and are each independently hydrogen, deuterium or a substituted or unsubstituted C1 to C10 alkyl group, and $R^1$ and $R^2$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof.

In some embodiments, in Chemical Formula 1, $Ar^3$ may be a cyclic group represented by one of Chemical Formula 2A to Chemical Formula 2D.

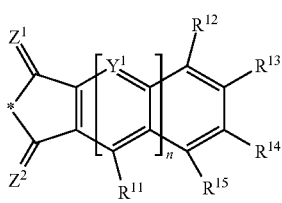

[Chemical Formula 2A]

In Chemical Formula 2A, $Z^1$ and $Z^2$ are the same or different and are each independently O, S, Se, or Te, $Y^1$ is N or $CR^a$ (wherein $R^a$ is hydrogen, deuterium, or a substituted or unsubstituted C1 to C10 alkyl group), $R^{11}$, $R^{12}$, $R^{13}$, $R^{14}$, and $R^{15}$ are the same or different and are each independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof or a pair of $R^{12}$ and $R^{13}$ or a pair of $R^{14}$ and $R^{15}$ is each independently linked with each other to provide a fused aromatic ring, n is 0 or 1, and

* is a linking point.

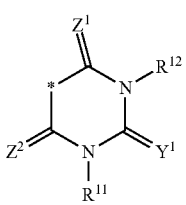

[Chemical Formula 2B]

In Chemical Formula 2B, $Z^1$ and $Z^2$ are the same or different and are each independently O, S, Se, or Te, $Y^1$ is O, S, Se, Te, or $C(R^a)(CN)$ (wherein $R^a$ is hydrogen, a cyano group (—CN), or a C1 to C10 alkyl group), $R^{11}$ and $R^{12}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

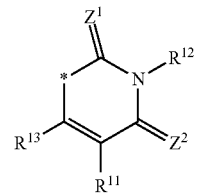

[Chemical Formula 2C]

In Chemical Formula 2C, $Z^1$ and $Z^2$ are the same or different and are each independently O, S, Se, or Te, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

[Chemical Formula 2D]

In Chemical Formula 2D, $Z^1$ and $Z^2$ are the same or different and are each independently O, S, Se, or Te, $Y^1$ is N or $CR^a$ (wherein $R^a$ is hydrogen, deuterium, or a substituted or unsubstituted C1 to C10 alkyl group), $G^1$ is —O—, —S—, —Se—, —Te—, —$SiR^xR^y$—, or —$GeR^zR^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking point.

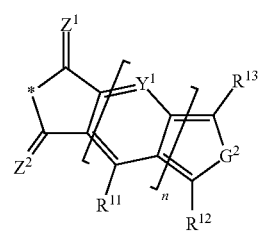

[Chemical Formula 2E]

In Chemical Formula 2E, $Z^1$ and $Z^2$ are the same or different and are each independently O, S, Se, or Te, $Y^1$ is N or $CR^a$ (wherein $R^a$ is hydrogen, deuterium, or a substituted or unsubstituted C1 to C10 alkyl group), $G^2$ is —O—, —S—, —Se—, —Te—, —SiR$^x$R$^y$—, or —GeR$^z$R$^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and n is 0 or 1, and

* is a linking point.

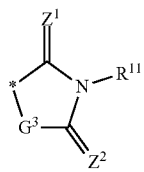

[Chemical Formula 2F]

In Chemical Formula 2F, $Z^1$ and $Z^2$ are the same or different and are each independently O, S, Se, or Te, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is —O—, —S—, —Se—, —Te—, —SiR$^x$R$^y$—, or —GeR$^z$R$^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group.

In some embodiments, $Z^1$ and $Z^2$ may both be oxygen in Chemical Formula 2B.

In some embodiments, in Chemical Formula 1, at least one of Ar$^1$ and Ar$^2$ may include a heteroatom of nitrogen (N), sulfur (S), or selenium (Se).

In some embodiments, in Chemical Formula 1, at least one of Ar$^1$ and Ar$^2$ may include a heteroatom of nitrogen (N), sulfur (S), or selenium (Se) at the position 1.

In some embodiments, in the N-containing heteroaromatic ring of Chemical Formula 1 (e.g.,

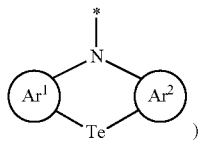

)

may be an electron donor moiety represented by one of Chemical Formula 4A to Chemical Formula 4G.

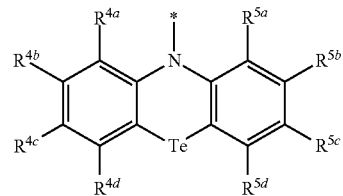

[Chemical Formula 4A]

In Chemical Formula 4A, $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring.

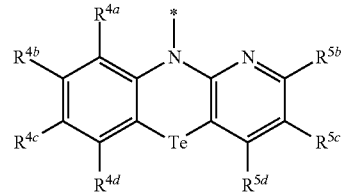

[Chemical Formula 4B]

In Chemical Formula 4B, $R^{4a}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5b}$ to $R^{5d}$ are linked with each other to provide a 5-membered aromatic ring or a 6-membered aromatic ring.

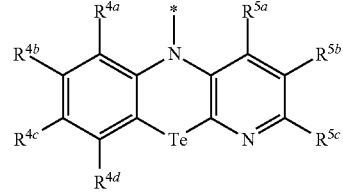

[Chemical Formula 4C]

In Chemical Formula 4C, $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^4$ are linked with each other to provide a 5-membered aromatic ring or a 6-membered aromatic ring and optionally two adjacent groups of $R^{5a}$ to $R^5$ are linked with each other to provide a 5-membered aromatic ring or a 6-membered aromatic ring.

[Chemical Formula 4D]

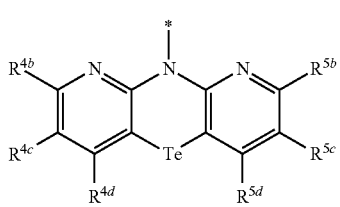

In Chemical Formula 4D, $R^{4b}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4b}$ to $R^{4d}$ are linked with each other to provide a 5-membered aromatic ring or a 6-membered aromatic ring and optionally two adjacent groups of $R^{5b}$ to $R^{5d}$ are linked with each other to provide a 5-membered aromatic ring or a 6-membered aromatic ring.

[Chemical Formula 4E]

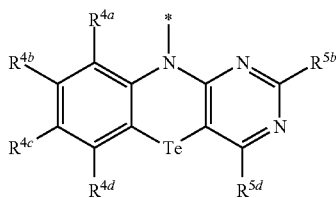

In Chemical Formula 4E, $R^{4a}$ to $R^{4d}$ and $R^{5b}$ and $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring.

[Chemical Formula 4F]

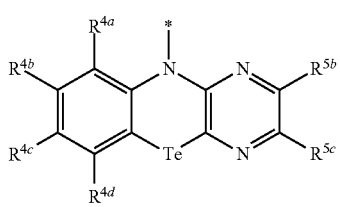

In Chemical Formula 4F, $R^{4a}$ to $R^{4d}$ and $R^{5b}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^4$ are linked with each other to provide a 5-membered aromatic ring or a 6-membered aromatic ring and optionally two adjacent groups of $R^{5b}$ and $R^{5c}$ are linked with each other to provide a 5-membered aromatic ring or a 6-membered aromatic ring.

[Chemical Formula 4G]

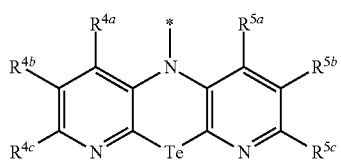

In Chemical Formula 4G, $R^{4a}$ to $R^{4c}$ and $R^{5a}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4c}$ are linked with each other to provide a 5-membered aromatic ring or a 6-membered aromatic ring and optionally two adjacent groups of $R^{5a}$ and $R^{5c}$ are linked with each other to provide a 5-membered aromatic ring or a 6-membered aromatic ring.

In some embodiments, the compound may have a maximum absorption wavelength ($\lambda_{max}$) in a wavelength region of greater than or equal to about 500 nm and less than about 600 nm In some embodiments, the compound may exhibit a light absorption curve having a full width at half maximum (FWHM) of about 50 nm to about 110 nm, in a thin film state.

In some embodiments, a difference between a melting point of the compound and a temperature (deposition temperature) at which 10 wt % of the initial weight is lost may be greater than or equal to about 3° C.

According to another embodiment, a photoelectric device (e.g., organic photoelectric device) includes a first electrode and a second electrode facing each other and an active layer between the first electrode and the second electrode. The active layer may include the compound represented by Chemical Formula 1.

According to another embodiment, an image sensor includes the photoelectric device.

In some embodiments, the image sensor may include a semiconductor substrate integrated with a plurality of first photo-sensing devices configured to sense light in a blue wavelength region and a plurality of second photo-sensing devices configured to sense light in a red wavelength region, and the photoelectric device on the semiconductor substrate and may be configured to selectively sense light in a green wavelength region.

In some embodiments, the first photo-sensing device and the second photo-sensing device may be stacked in a vertical direction in the semiconductor substrate.

In some embodiments, the image sensor may further include a color filter layer including a blue filter configured to selectively absorb light in a blue wavelength region and a red filter configured to selectively absorb light in a red wavelength region.

In some embodiments, the photoelectric device in the image sensor may be a green photoelectric device and an organic photoelectric device. The image sensor may further include a blue photoelectric device configured to selectively absorb light in a blue wavelength region, and a red photoelectric device configured to selectively absorb light in a red wavelength region. The blue photoelectric device and the green photoelectric device may be stacked.

According to another embodiment, an electronic device includes the image sensor.

The compound may selectively absorb light in a green wavelength region and may have thermal stability. The compound improves efficiency by increasing wavelength selectivity of the green wavelength region and provides photoelectric devices, image sensors and electronic devices that do not deteriorate performance even at high temperature processes due to improved thermal stability.

DETAILED DESCRIPTION

Figure 1:
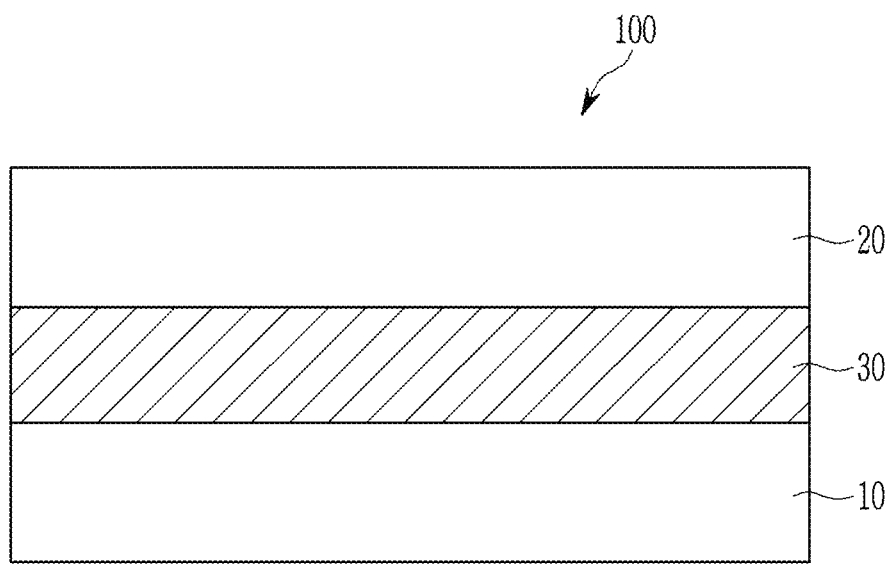
FIG. 1 is a cross-sectional view showing a photoelectric device according to an embodiment.

Example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; A and B; A and C; B and C; or A, B and C).

As used herein, when specific definition is not otherwise provided, "substituted" refers to replacement of a hydrogen of a compound or a functional group by a substituent selected from a halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, =S, and a combination thereof.

As used herein, when specific definition is not otherwise provided, "hetero" refers to one including 1 to 3 heteroatoms selected from N, O, S, Se, Te, P, and Si.

As used herein, "alkyl group" refers to a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, "aryl group" refers to a substituent including all element of the functional group having p-orbitals which form conjugation, and may be a monocyclic, polycyclic or fused ring polycyclic (e.g., rings sharing adjacent pairs of carbon atoms) functional group.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as =$CR^{x'}$—$(CR^{x}R^{y})_p$—$CR^{y'}(CN)_2$ wherein $R^{x}$, $R^{y}$, $R^{x'}$, and $R^{y'}$ are each independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "combination thereof" refers to at least two substituents bound to each other by a single bond or a C1 to C10 alkylene group, or at least two fused substituents.

As used herein, "hydrocarbon cyclic group" refers to a fused ring of an aromatic ring (arene ring) and a nonaromatic ring (alicyclic ring) and may include, for example a fused ring which is formed by linking at least one aromatic ring (arene ring) such as a C6 to C30 aryl group, a C6 to C20 aryl group, or a C6 to C10 aryl group with at least one nonaromatic ring (alicyclic ring) such as a C3 to C30 cycloalkyl group, a C3 to C20 cycloalkyl group, or a C3 to C10 cycloalkyl group.

As used herein, "heterocyclic group" refers to a cyclic group including a heteroatom selected from N, O, S, Se, Te, P, and Si instead of 1 to 3 carbon atoms in a cyclic group selected from an arene group (e.g., C6 to C30 aryl group, C6 to C20 aryl group or C6 to C10 aryl group), an alicyclic hydrocarbon group (e.g., C3 to C30 cycloalkyl group, C3 to C20 cycloalkyl group or C3 to C10 cycloalkyl group), or a fused ring thereof. At least one carbon atom of the heterocyclic group may also be substituted with a thiocarbonyl group (C=S).

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, Se, Te, P and Si in a cyclic group.

As used herein, "C6 to C30 aromatic hydrocarbon group" includes a C6 to C30 aryl group such as a phenyl group, a naphthyl group, a C6 to C30 arylene group, and the like, but is not limited thereto.

As used herein, "aliphatic hydrocarbon group" may include, for example, a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited to.

As used herein, "5-membered aromatic ring" refers to a 5-membered ring group (e.g., C5 aryl group) having a conjugation structure or a 5-membered heterocyclic group (e.g., C2 to C4 heteroaryl group) having a conjugation structure. As used herein, "6-membered aromatic ring" refers to a 6-membered ring group (e.g., C6 aryl group) having a conjugation structure or a 6-membered heterocyclic group (e.g., C2 to C5 heteroaryl groups) having a conjugation structure, but is not limited thereto. The aromatic ring may include the 5-membered aromatic ring or the 6-membered aromatic ring, but is not limited thereto.

Hereinafter, a compound according to an embodiment is described. The compound is represented by Chemical Formula 1.

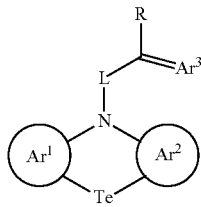

[Chemical Formula 1]

In Chemical Formula 1, $Ar^3$ is a substituted or unsubstituted C6 to C30 hydrocarbon cyclic group having two functional groups of C=O, C=S, C=Se, or C=Te, a substituted or unsubstituted C6 to C30 heterocyclic group having a functional group of C=O, C=S, C=Se, or C=Te, or a fused ring thereof, R is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, $Ar^1$ and $Ar^2$ are each independently a substituted or unsubstituted C6 to C30 arene group, a substituted or unsubstituted C3 to C30 heteroarene group, or a condensed ring thereof, and L is a linker represented by Chemical Formula A or Chemical Formula B:

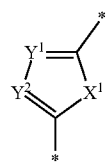

[Chemical Formula A]

wherein, in Chemical Formula A,
$X^1$ is —Se—, —Te—, —O—, —S(=O)—, —S(=O)$_2$—, —NR$^a$—, —SiR$^b$R$^c$—, or —GeR$^d$R$^e$—,
$Y^1$ and $Y^2$ are the same or different and are each independently CR$^f$ or N,
when $Y^1$ and $Y^2$ are CR$^y$, $Y^1$ and $Y^2$ are each independently present or are linked with each other to provide a ring,
$R^a$ to $R^f$ are the same or different and are each independently hydrogen, deuterium or a substituted or unsubstituted C1 to C10 alkyl group, and
* is a linking point,

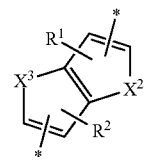

[Chemical Formula B]

wherein, in Chemical Formula B
$X^2$ and $X^3$ are the same or different and are each independently —S—, —Se—, —Te—, —O—, —S(=O)—, —S(=O)$_2$—, —NR$^a$—, —SiR$^b$R$^c$—, or —GeR$^d$R$^e$—,
$R^a$ to $R^e$ are the same or different and are each independently hydrogen, deuterium or a substituted or unsubstituted C1 to C10 alkyl group, and
$R^1$ and $R^2$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof.

The compound represented by Chemical Formula 1 includes an N-containing heteroaromatic ring as an electron donor moiety, a moiety represented by Chemical Formula A or Chemical Formula B as a linker, and an electron acceptor moiety represented by Ar$^3$.

In Chemical Formula 1, the cyclic group represented by Ar$^3$ includes two functional groups selected from C=O, C=S, C=Se, and C=Te as an electron acceptor moiety. Ar$^3$ may be a substituted or unsubstituted C6 to C30 hydrocarbon cyclic group having two functional groups selected from C=O, C=S, C=Se, and C=Te, a substituted or unsubstituted C6 to C30 heterocyclic group having a functional group selected from C=O, C=S, C=Se, and C=Te, or a fused ring thereof. In an embodiment, Ar$^3$ may be a substituted or unsubstituted 5-membered aromatic ring having two functional groups selected from C=O, C=S, C=Se, and C=Te, a substituted or unsubstituted 6-membered aromatic ring having two functional groups selected from C=O, C=S, C=Se, and C=Te, or a condensed ring of two or more.

In Chemical Formula 1, Ar³ may be a cyclic group represented by one of Chemical Formula 2A to Chemical Formula 2D.

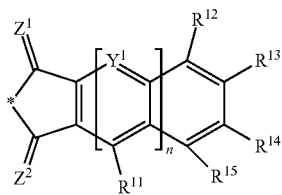

[Chemical Formula 2A]

In Chemical Formula 2A, $Z^1$ and $Z^2$ are the same or different and are each independently O, S, Se, or Te, $Y^1$ is N or $CR^a$ (wherein $R^a$ is hydrogen, deuterium, or a substituted or unsubstituted C1 to C10 alkyl group), $R^{11}$, $R^{12}$, $R^{13}$, $R^{14}$, and $R^{15}$ are the same or different and are each independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof or a pair of $R^{12}$ and $R^{13}$ or a pair of $R^{14}$ and $R^{15}$ is each independently linked with each other to provide a fused aromatic ring, n is 0 or 1, and

* is a linking point.

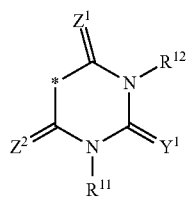

[Chemical Formula 2B]

In Chemical Formula 2B, $Z^1$ and $Z^2$ are the same or different and are each independently O, S, Se, or Te, $Y^1$ is O, S, Se, Te, or $C(R^a)(CN)$ (wherein $R^a$ is hydrogen, a cyano group (—CN), or a C1 to C10 alkyl group), $R^{11}$ and $R^{12}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

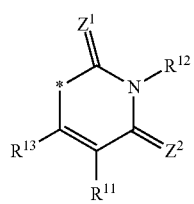

[Chemical Formula 2C]

In Chemical Formula 2C, $Z^1$ and $Z^2$ are the same or different and are each independently O, S, Se, or Te, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

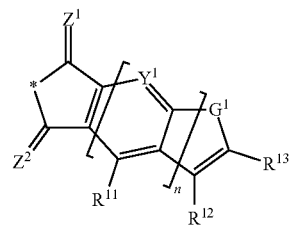

[Chemical Formula 2D]

In Chemical Formula 2D, $Z^1$ and $Z^2$ are the same or different and are each independently O, S, Se, or Te, $Y^1$ is N or $CR^a$ (wherein $R^a$ is hydrogen, deuterium, or a substituted or unsubstituted C1 to C10 alkyl group), $G^1$ is —O—, —S—, —Se—, —Te—, —SiR$^x$R$^y$—, or —GeR$^z$R$^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking point.

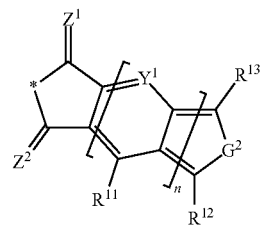

[Chemical Formula 2E]

In Chemical Formula 2E, $Z^1$ and $Z^2$ are the same or different and are each independently O, S, Se, or Te, $Y^1$ is N or $CR^a$ (wherein $R^a$ is hydrogen, deuterium, or a substituted or unsubstituted C1 to C10 alkyl group), $G^2$ is —O—, —S—, —Se—, —Te—, —SiR$^x$R$^y$—, or —GeR$^z$R$^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and n is 0 or 1, and

* is a linking point.

[Chemical Formula 2F]

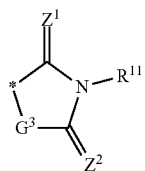

In Chemical Formula 2F, $Z^1$ and $Z^2$ are the same or different and are each independently O, S, Se, or Te, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is —O—, —S—, —Se—, —Te—, —SiR$^x$R$^y$—, or —GeR$^z$R$^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group.

The cyclic group represented by Chemical Formula 2A may be for example a cyclic group represented by Chemical Formula 2A-1 or 2A-2.

[Chemical Formula 2A-1]

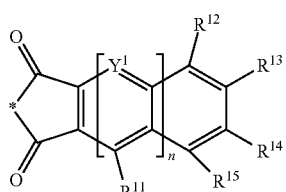

[Chemical Formula 2A-2]

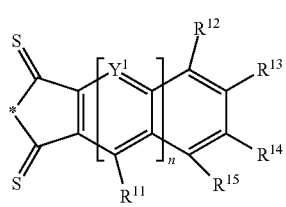

In Chemical Formula 2A-2 and Chemical Formula 2A-3, $Y^1$, $R^{11}$, n, $R^{11}$, $R^{12}$, $R^{13}$, $R^{14}$, and $R^{15}$ are the same as in Chemical Formula 2A.

The cyclic group represented by Chemical Formula 2A may be represented by Chemical Formula 2A-3 when the pair of $R^{12}$ and $R^{13}$ and/or the pair of $R^{14}$ and $R^{15}$ are each independently linked with each other to provide a fused aromatic ring.

[Chemical Formula 2A-3]

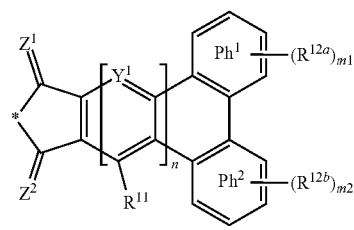

In Chemical Formula 2A-3, $Z^1$, $Z^2$, $Y^1$, $R^{11}$, and n are the same as in Chemical Formula 2A, $R^{12a}$ and $R^{12b}$ are each independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m1 and m2 are each independently an integer of 0 to 4, Ph1 and Ph2 refer to fused phenylene rings and one of Ph1 and Ph2 may be optionally omitted.

The cyclic group represented by Chemical Formula 2B may be, for example, a cyclic group represented by Chemical Formula 2B-1, 2B-2, or 2B-3.

[Chemical Formula 2B-1]

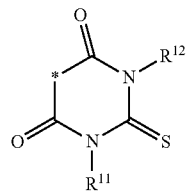

[Chemical Formula 2B-2]

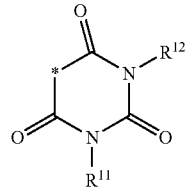

[Chemical Formula 2B-3]

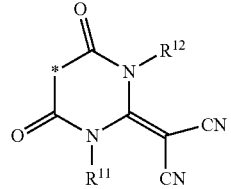

In Chemical Formulae 2B-1, 2B-2, and 2B-3, $R^{11}$ and $R^{12}$ are the same as in Chemical Formula 2B.

The cyclic group represented by Chemical Formula 2C may be, for example, a cyclic group represented by 2C-1 or 2C-3.

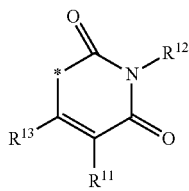

[Chemical Formula 2C-1]

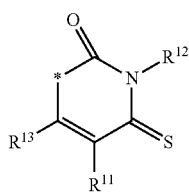

[Chemical Formula 2C-2]

In Chemical Formulae 2C-1 and 2C-2, $R^{11}$ to $R^{13}$ are the same as in Chemical Formula 2C.

$Ar^1$ and $Ar^2$ of the N-containing heteroaromatic ring are linked by Te to provide a single conjugation structure as a whole to improve thermal stability of the compound. This conjugation structure may be formed by fusing three or four 5- or 6-membered aromatic rings, but is not limited thereto.

$Ar^1$ and $Ar^2$ may be a substituted or unsubstituted C6 to C30 arene group, a substituted or unsubstituted C3 to C30 heteroarene group, or a condensed ring thereof in which aromatic rings are fused with each other, for example a substituted or unsubstituted C6 to C20 arene group, a substituted or unsubstituted C3 to C20 heteroarene group, or a condensed ring thereof.

In an embodiment, the arene group may be benzene, naphthalene, and anthracene. The heteroarene group may be pyrrole, pyrazole, imidazole, oxazole, isoxazole, thiazole, isothiazole, pyridine, pyridazine, pyrimidine, pyrazine, indole, quinoline, isoquinoline, naphthyridine, cinnoline, quinazoline, phthalazine, benzotriazine, pyridopyrazine, pyridopyrimidine, pyridopyridazine, thiophene, benzothiophene, selenophene, or benzoselenophene.

In Chemical Formula 1, $X^1$ and $X^2$ of the linker (L) represented by Chemical Formula A or Chemical Formula B; $Z^1$ and $Z^2$ (O, S, Se and Te) in the electron acceptor moiety may increase an intramolecular interaction to improve absorption intensity at desired and/or alternatively predetermined wavelengths.

In the linker represented by Chemical Formula A, when $Y^1$ and $Y^2$ are $CR^y$, $Y^1$ and $Y^2$ may be linked with each other to provide a ring. In this case, the linker represented by Chemical Formula A may be represented by Chemical Formula A-1 or Chemical Formula A-2.

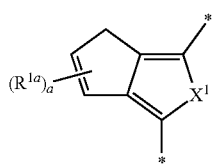

[Chemical Formula A-1]

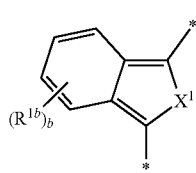

[Chemical Formula A-2]

In Chemical Formula A-1 and Chemical Formula A-2, $R^{1a}$ and $R^{1b}$ is hydrogen, a C1 to C10 alkyl group, a C6 to C10 aryl group, a C2 to C10 heteroaryl group, or a halogen, and a and b are each independently an integer of 1 to 4.

The linker represented by Chemical Formula B may be represented by Chemical Formula B-1.

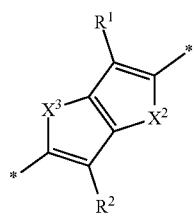

[Chemical Formula B-1]

In Chemical Formula B-1

$X^2$, $X^3$, $R^1$, and $R^2$ are the same as in Chemical Formula B.

In Chemical Formula 1, at least one of AO and Are may include a heteroatom of nitrogen (N), sulfur (S), or selenium (Se). In an embodiment, the heteroatom may include a heteroatom selected from nitrogen (N), sulfur (S), and selenium (Se) present at position 1 with respect to the nitrogen (N). In this case, $X^1$ and $X^2$ of the linker (L) represented by Chemical Formula A or Chemical Formula B; $Z^1$ and $Z^2$ (O, S, Se, or Te) in the electron acceptor moiety may increase an intramolecular interaction to improve absorption intensity at desired and/or alternatively predetermined wavelengths.

The electron donor moiety of the N-containing heteroaromatic ring of Chemical Formula 1 may be represented by one of Chemical Formula 4A to Chemical Formula 4G.

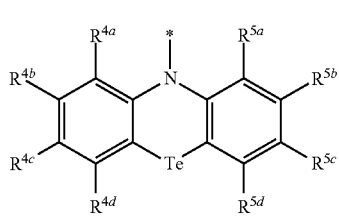

[Chemical Formula 4A]

In Chemical Formula 4A, $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring.

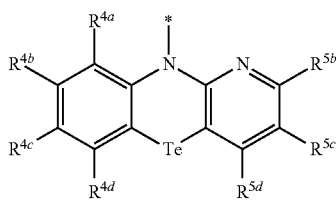

[Chemical Formula 4B]

In Chemical Formula 4B, $R^{4a}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^4$ are linked with each other to provide a 5-membered aromatic ring or a 6-membered aromatic ring and optionally two adjacent groups of $R^{5b}$ to $R^{5d}$ are linked with each other to provide a 5-membered aromatic ring or a 6-membered aromatic ring.

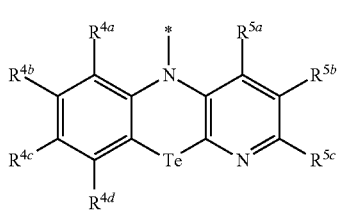

[Chemical Formula 4C]

In Chemical Formula 4C, $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring.

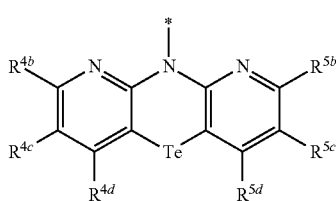

[Chemical Formula 4D]

In Chemical Formula 4D, $R^{4b}$ to $R^{4d}$ and $R^{5b}$ to $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4b}$ to $R^{4d}$ are linked with each other to provide a 5-membered aromatic ring or a 6-membered aromatic ring and optionally two adjacent groups of $R^{5b}$ to $R^{5d}$ are linked with each other to provide a 5-membered aromatic ring or a 6-membered aromatic ring.

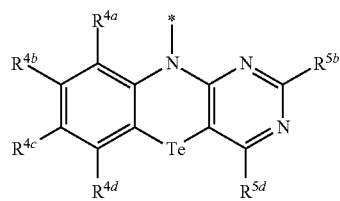

[Chemical Formula 4E]

In Chemical Formula 4E, $R^{4a}$ to $R^4$ and $R^{5b}$ and $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^4$ are linked with each other to provide a 5-membered aromatic ring or a 6-membered aromatic ring.

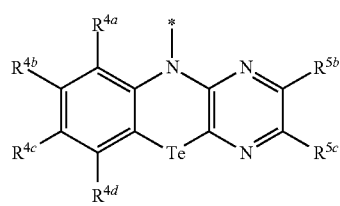

[Chemical Formula 4F]

In Chemical Formula 4F, $R^{4a}$ to $R^{4d}$ and $R^{5b}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4b}$ are linked with each other to provide a 5-membered aromatic ring or a 6-membered aromatic ring and optionally two adjacent groups of $R^{5b}$ and $R^{5c}$ are linked with each other to provide a 5-membered aromatic ring or a 6-membered aromatic ring.

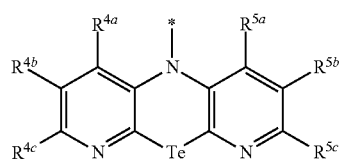

[Chemical Formula 4G]

In Chemical Formula 4G, $R^{4a}$ to $R^{4b}$ and $R^{5a}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4b}$ are linked with each other to provide a 5-membered aromatic ring or a 6-membered aromatic ring and optionally two adjacent groups of $R^{5a}$ and $R^x$ are linked with each other to provide a 5-membered aromatic ring or a 6-membered aromatic ring.

Specific examples of the compound of Chemical Formula 1 may be compounds of Chemical Formula 5A, Chemical Formula 5B, Chemical Formula 5C, Chemical Formula 5D, Chemical Formula 5E, and Chemical Formula 5F, but are not limited thereto.

[Chemical Formula 5A]

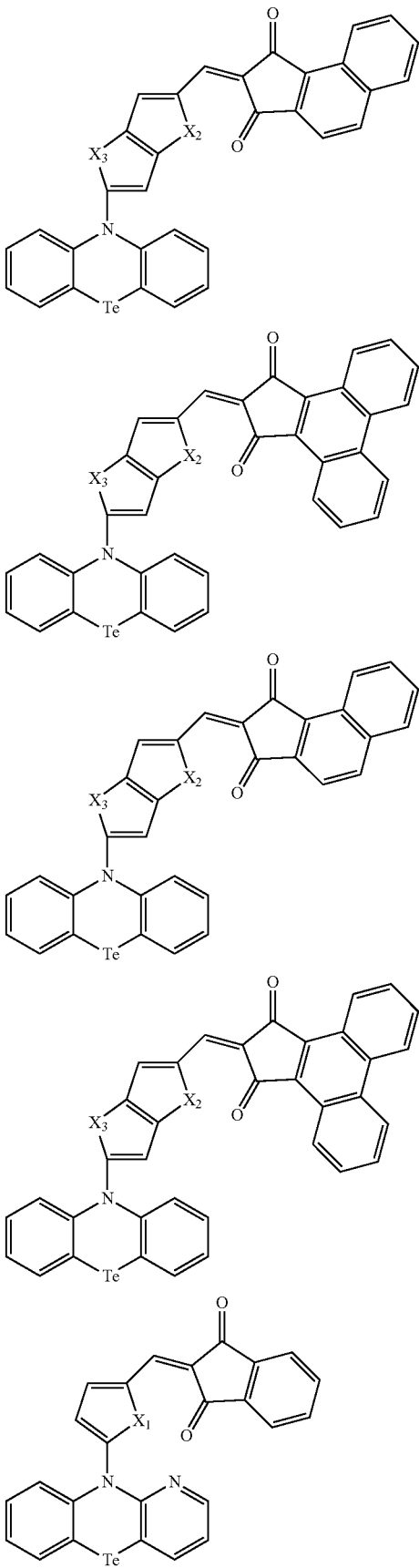

23
-continued
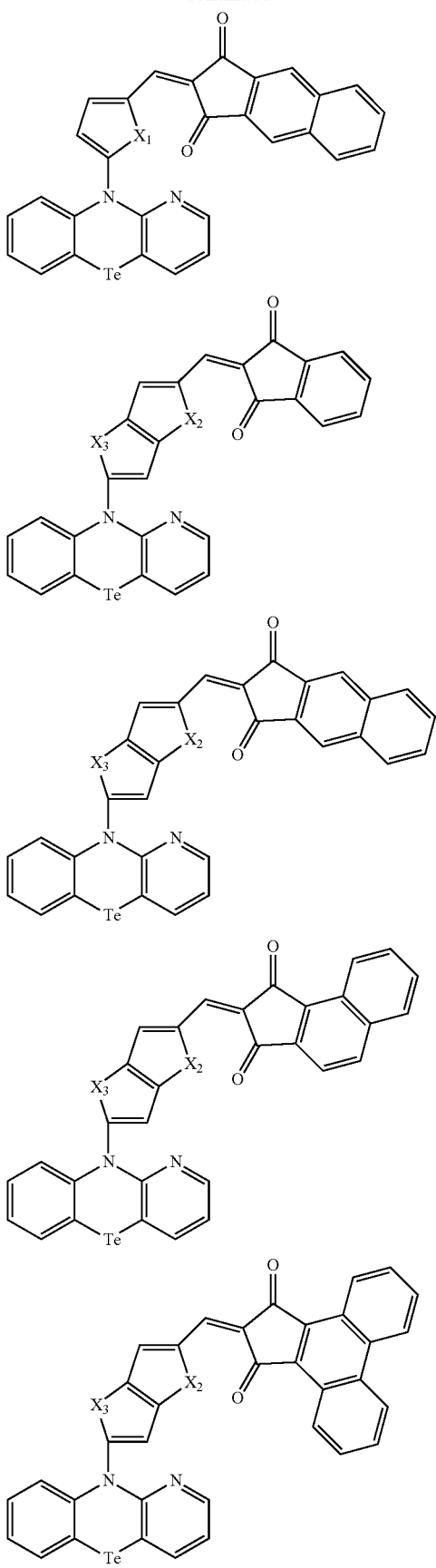
24
-continued
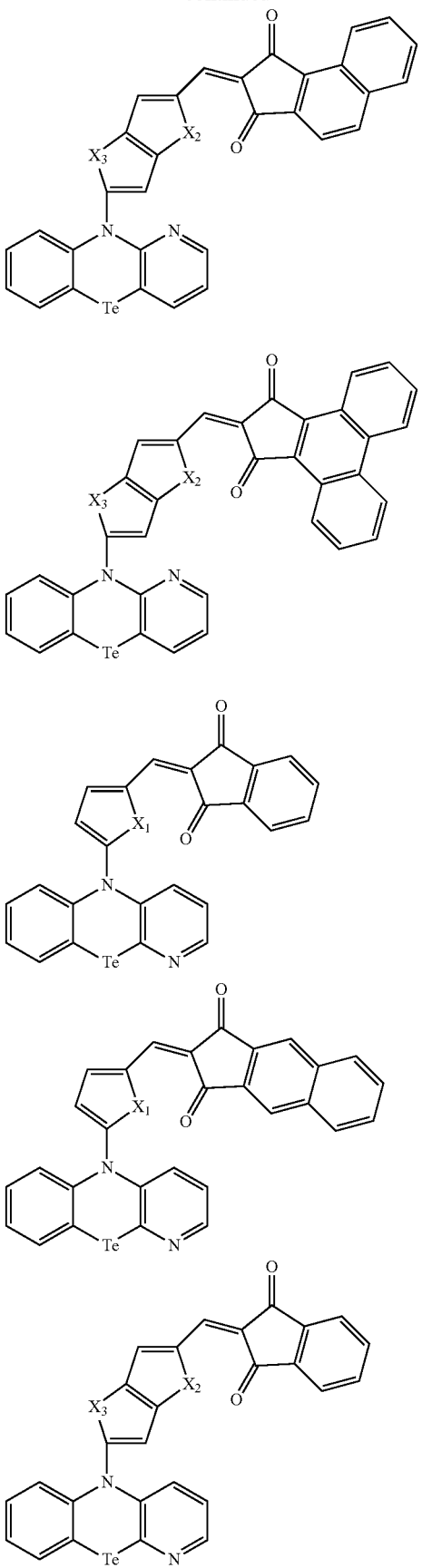

-continued
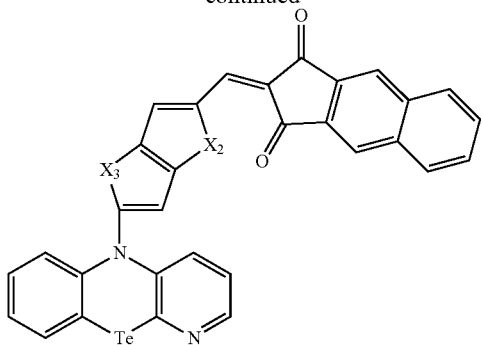
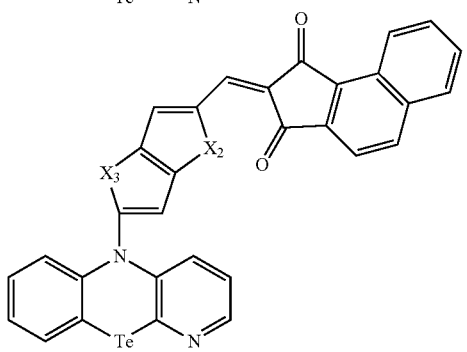
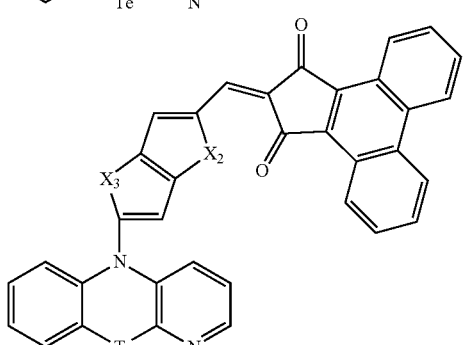
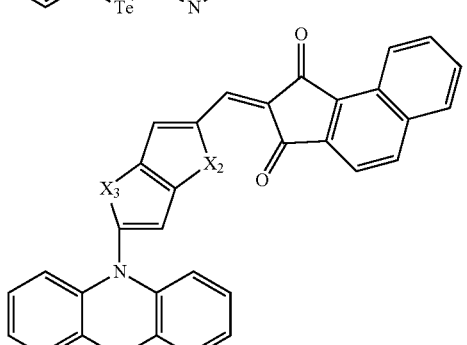
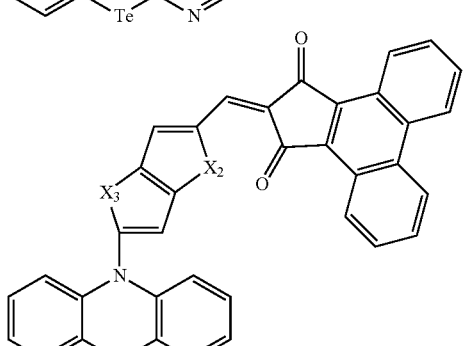
-continued
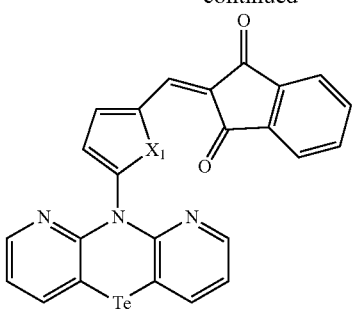
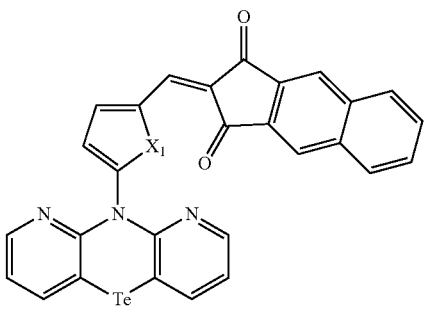
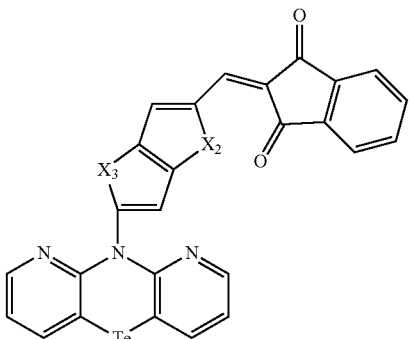
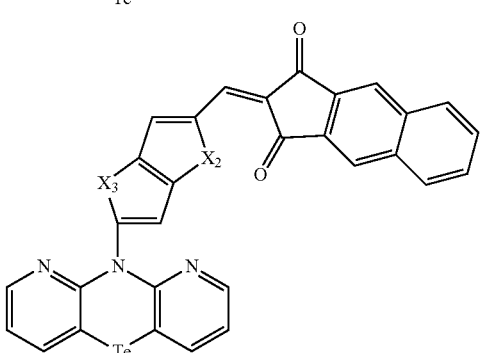
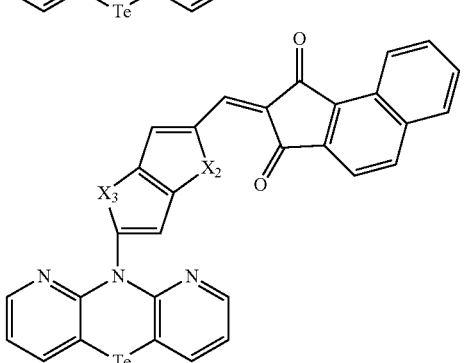

27
-continued
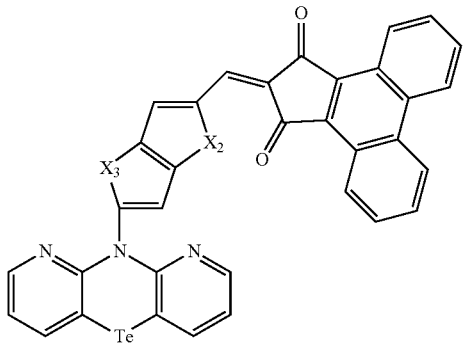
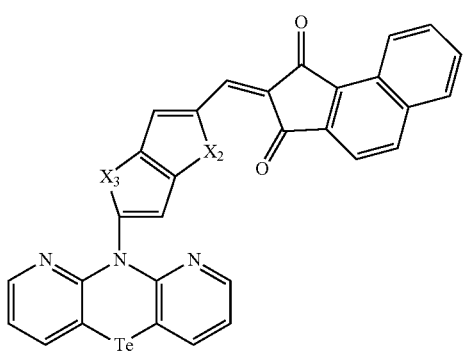
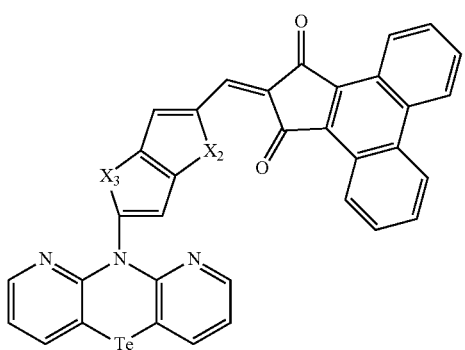
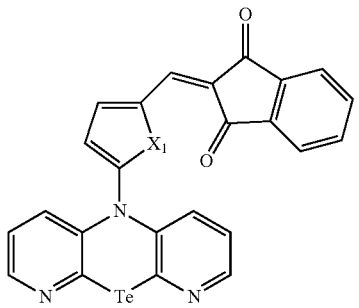
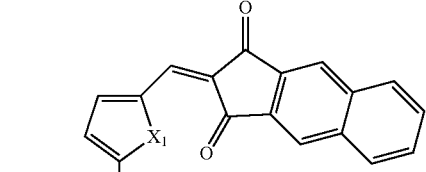
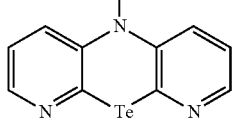
28
-continued
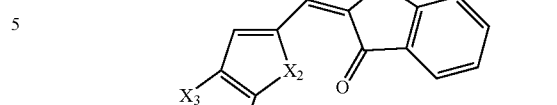
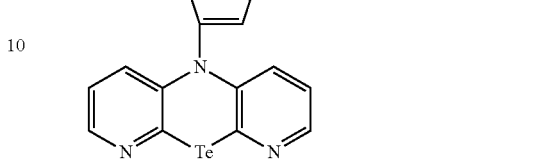
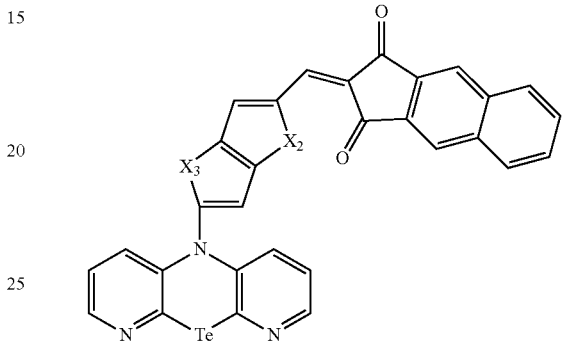
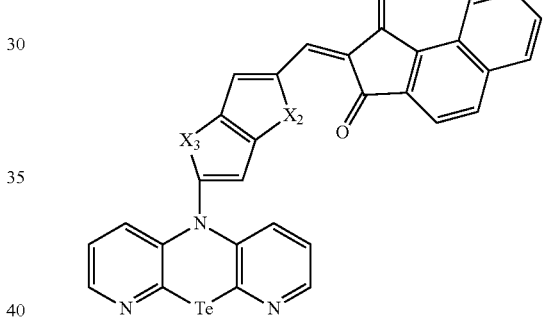
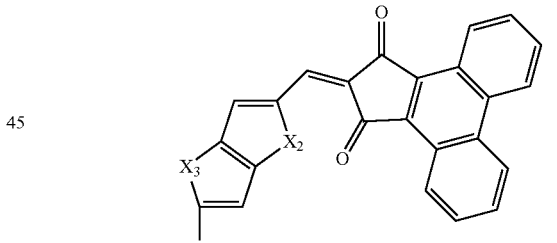
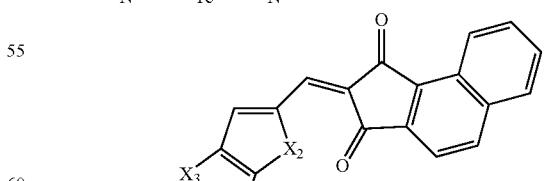
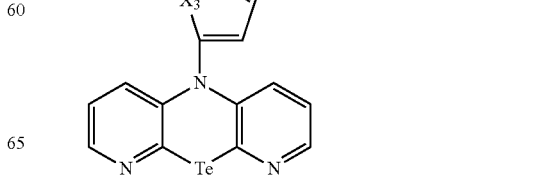

-continued

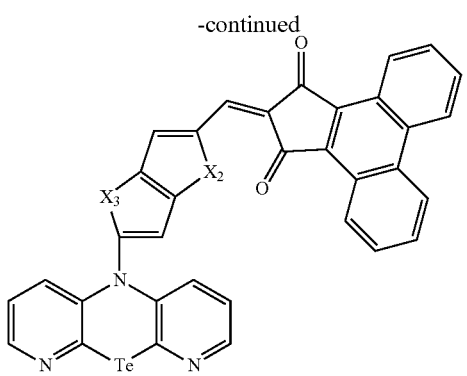

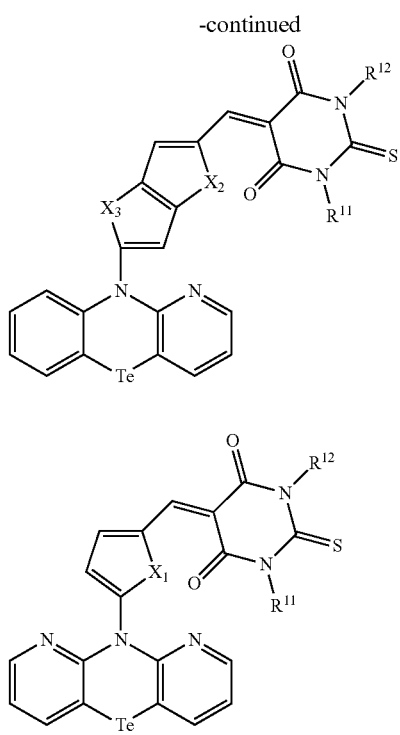

In Chemical Formula 5A,
X¹ is the same as in Chemical Formula A,
X² and X³ are the same as in Chemical Formula B, and
hydrogen of each aromatic ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 5B]

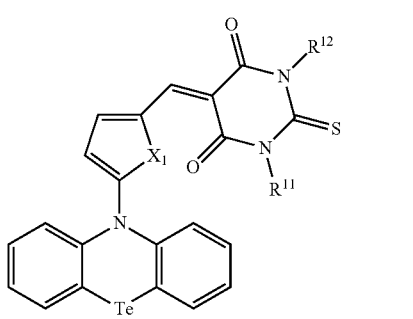

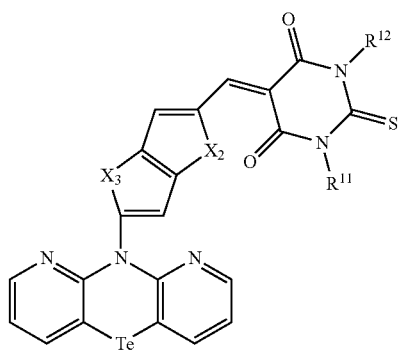

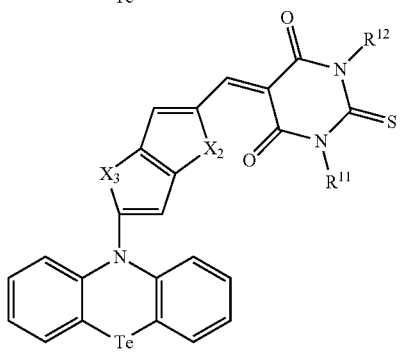

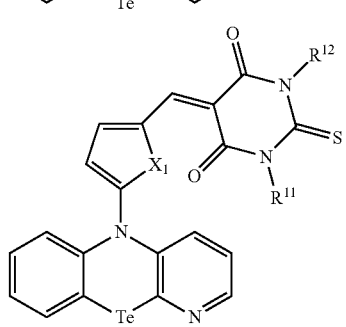

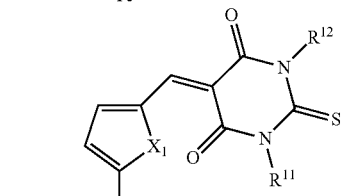

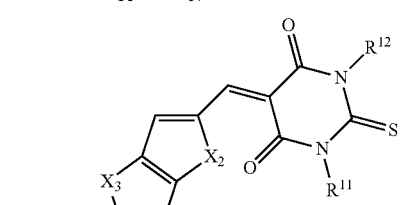

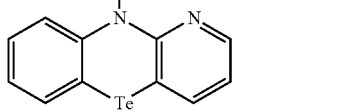

-continued

31

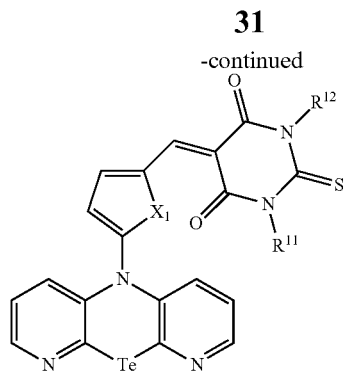

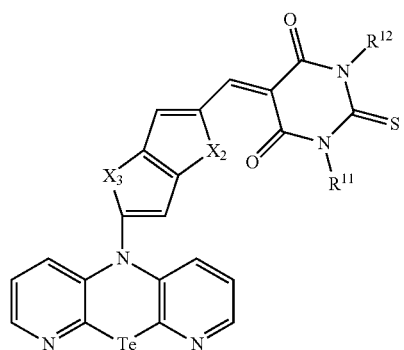

In Chemical Formula 5B, $X^1$ is the same as in Chemical Formula A, $X^2$ and $X^3$ are the same as in Chemical Formula B, $R^{11}$ and $R^{12}$ are the same as in Chemical Formula 2B, hydrogen of each aromatic ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 5C]

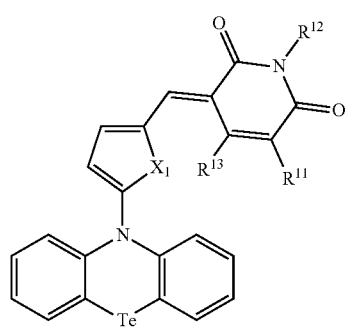

-continued

32

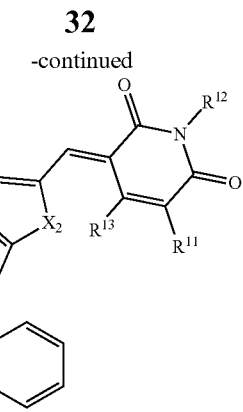

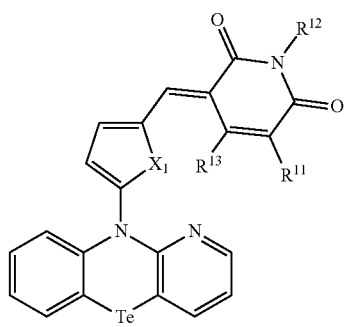

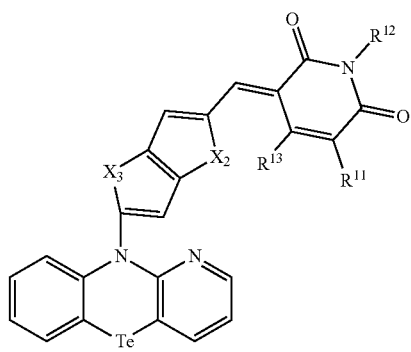

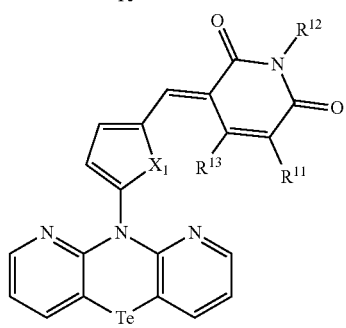

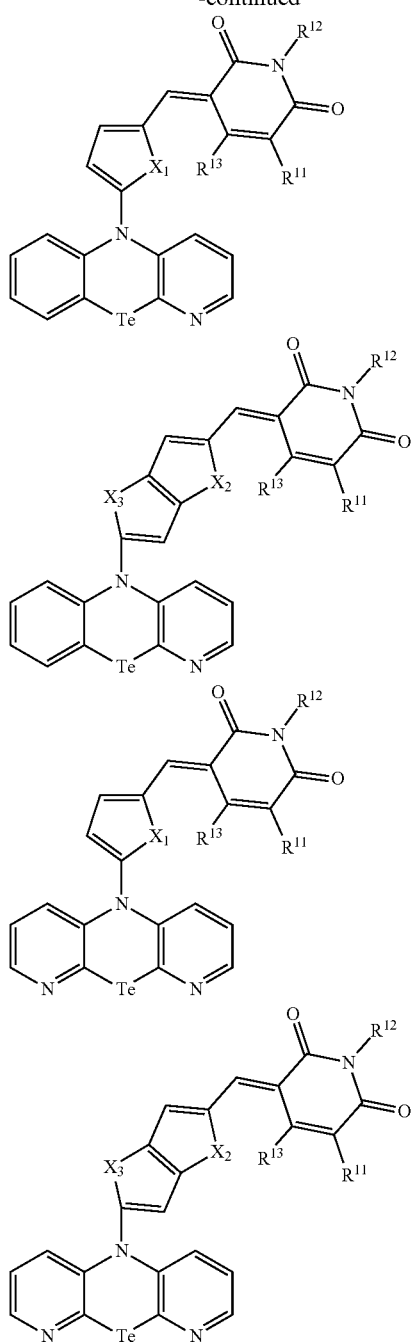
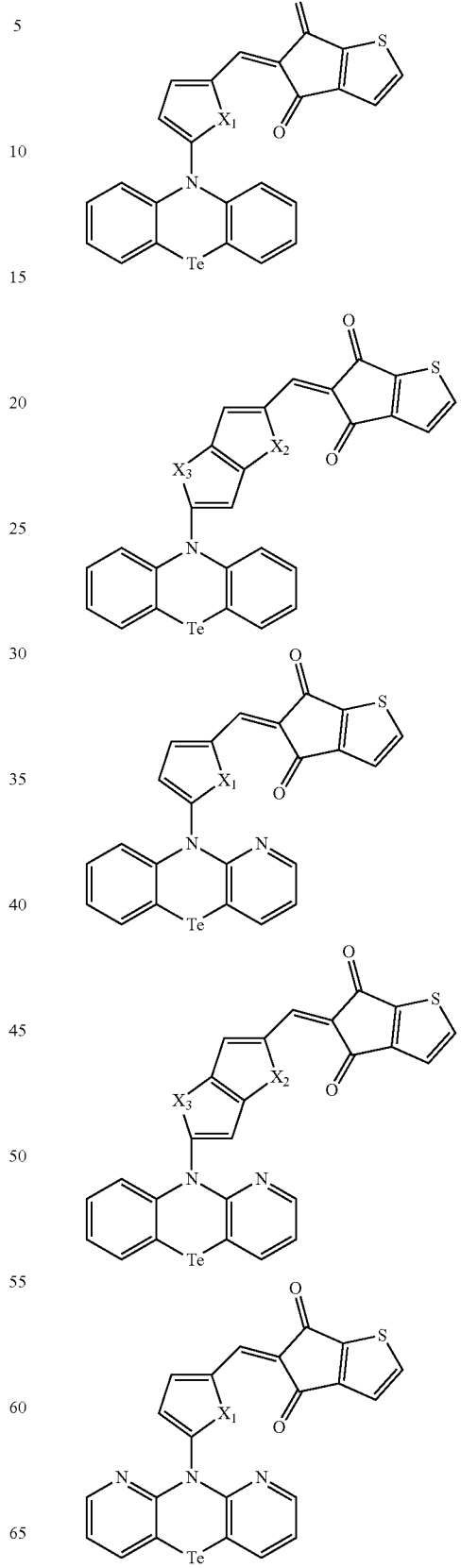

[Chemical Formula 5D]

In Chemical Formula 5C,

X¹ is the same as in Chemical Formula A,

X² and X³ are the same as in Chemical Formula B,

R¹¹ to R¹³ are the same as in Chemical Formula 2C, hydrogen of each aromatic ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

-continued

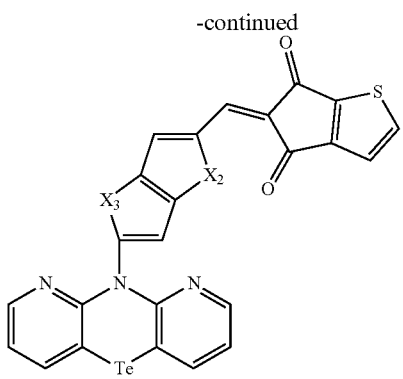

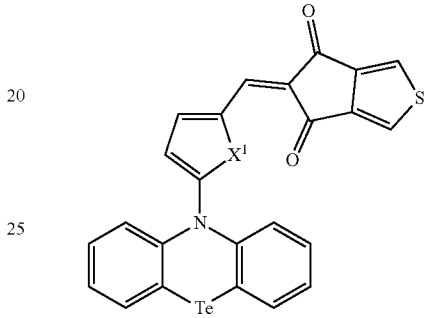

In Chemical Formula 5D,

X¹ is the same as in Chemical Formula A,

X² and X³ are the same as in Chemical Formula B, hydrogen of each aromatic ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 5E]

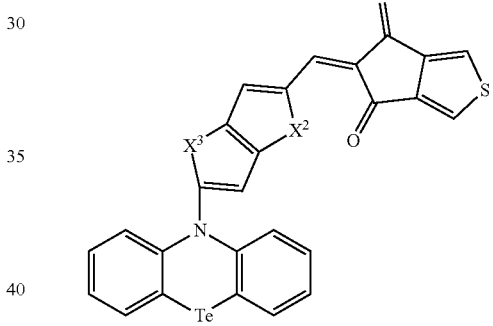

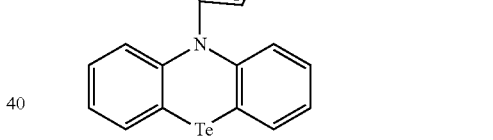

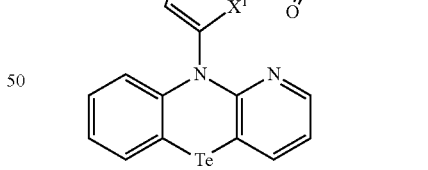

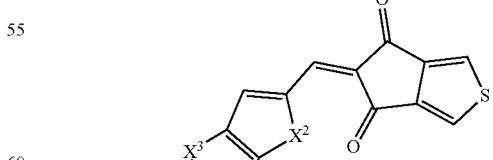

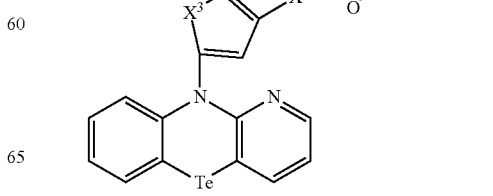

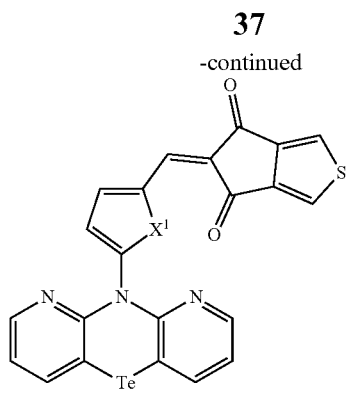
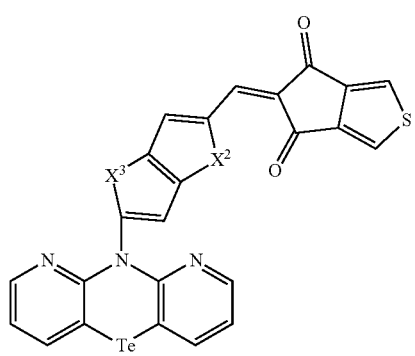
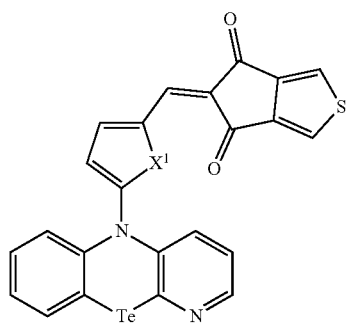
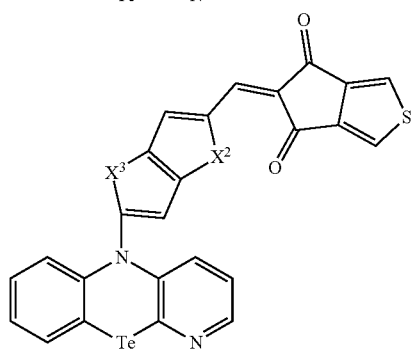
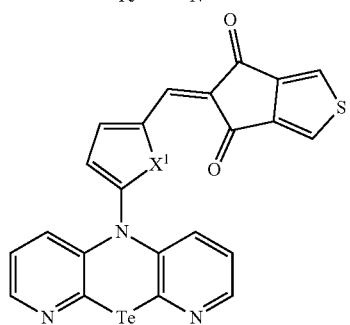

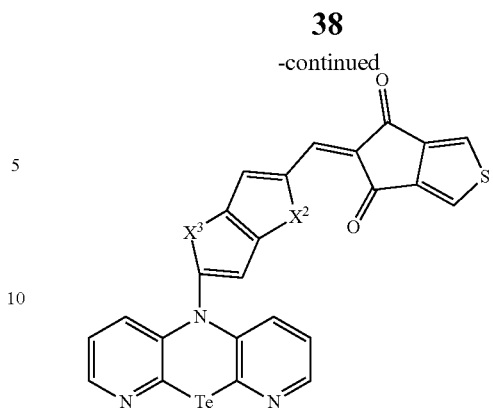

In Chemical Formula 5E, $X^1$ is the same as in Chemical Formula A, $X^2$ and $X^3$ are the same as in Chemical Formula B, hydrogen of each aromatic ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 5F]

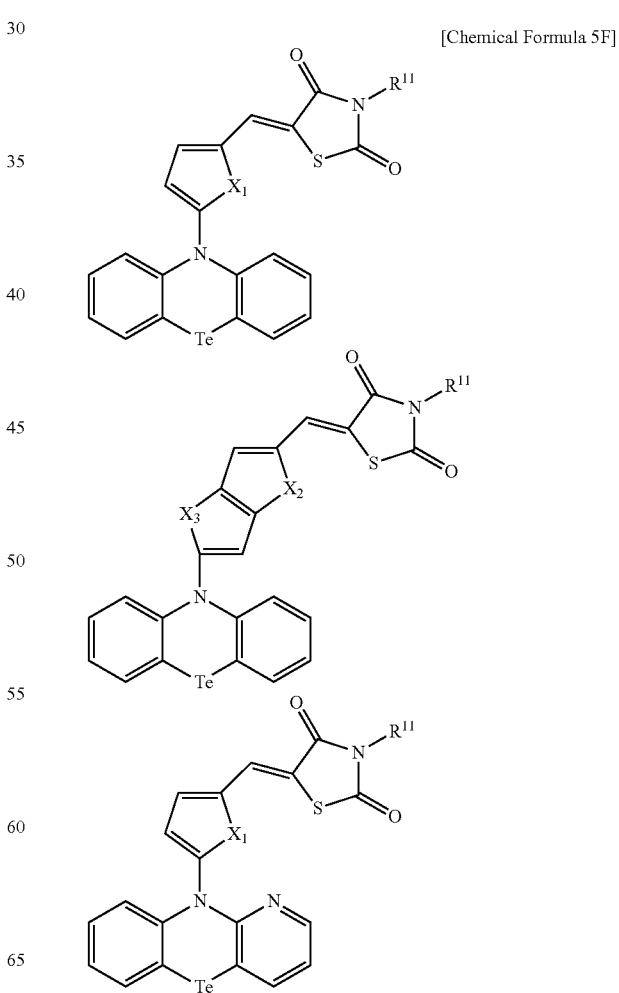

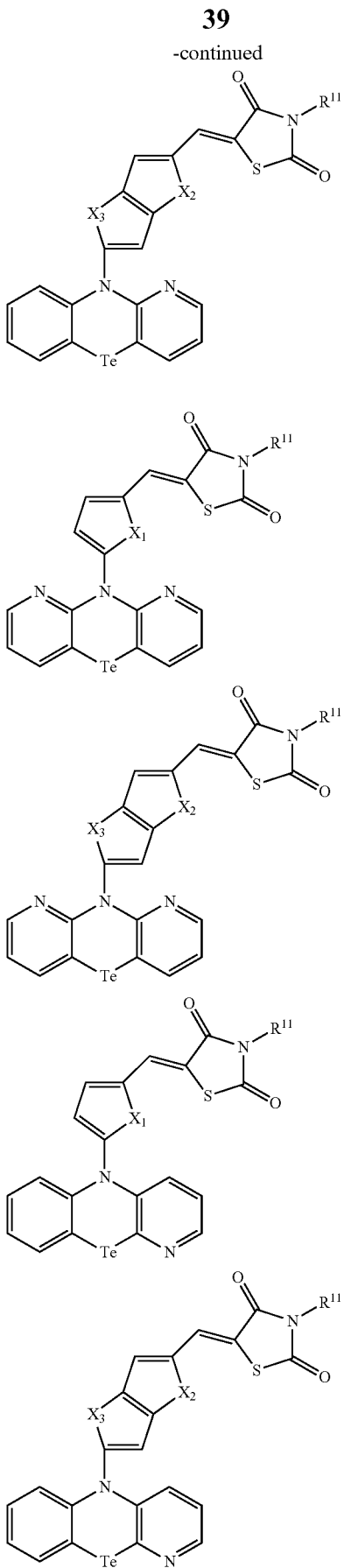

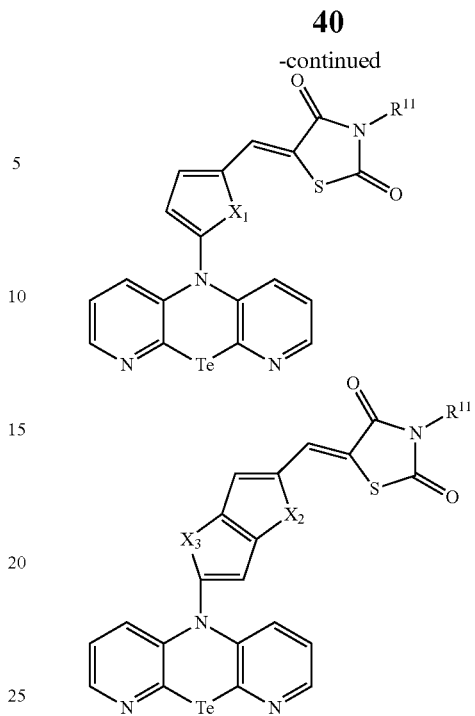

In Chemical Formula 5F, $X^1$ is the same as in Chemical Formula A, $X^2$ and $X^3$ are the same as in Chemical Formula B, $R^{11}$ is the same as in Chemical Formula 2F hydrogen of each aromatic ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

The compound is a compound selectively absorbing light in a green wavelength region, and may have a maximum absorption wavelength (λmax) in a wavelength region of about 500 nm to about 600 nm, for example greater than or equal to about 530 nm, greater than or equal to about 535 nm, or greater than or equal to about 540 nm and less than or equal to about 590 nm or less than or equal to about 580 nm.

The compound may exhibit a light absorption curve having a full width at half maximum (FWHM) of about 50 nm to about 110 nm, for example about 50 nm to about 100 nm. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by deposition. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. In this respect, the compound has a melting point higher than the deposition temperature. Because a difference between the melting point and the deposition temperature may be for example greater than or equal to about 3° C., greater than or equal to about 10° C., the compound may be desirably used in the deposition process.

In more detail, the donor-acceptor type material represented by Chemical Formula 1 may be thermally decomposed at the melting point ($T_m$) of the material because the melting point ($T_m$) is similar to the decomposition temperature ($T_d$). If the temperature (sublimation temperature, deposition temperature, $T_s$) at which a film is formed by vacuum deposition is higher than $T_m$, decomposition occurs more preferentially than sublimation (deposition), and thus a normal device cannot be manufactured. Because it is impossible to produce a stable image sensor with such materials, $T_m$ is required to be higher than $T_s$. In an embodiment, ($T_m$-$T_s$) may be in the range of ($T_m$-$T_s$)≥3° C. and for example ($T_m$-$T_s$)≥10° C.

In addition, a micro lens array (MLA) needs to be formed to concentrate light after manufacturing an organic photoelectric device during manufacture of an image sensor. This micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal agitation due to a heat treatment, but even a material having a firm molecule structure may not have the thermal agitation and be limited and/or prevented from the deterioration by the heat treatment. The compound may be suppressed from the thermal vibration of molecules due to a conjugation structure (Te-containing linkage structure of Chemical Formula 1) in the donor moiety and thus may be stably maintained during the MLA heat treatment and secure process stability.

The compound may be a p-type semiconductor compound.

Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the appropriate HOMO-LUMO level of the compound, when the compound has a HOMO level ranging from about 5.2 eV to about 5.8 eV, and an energy bandgap ranging from about 1.4 eV to about 2.6 eV, the LUMO level of the compound is in a range of about 3.8 eV to about 3.2 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a stably depositable compound is desirable and thus the compound has a molecular weight of about 300 g/mol to about 1500 g/mol. However, even though the compound has a molecular weight out of the range, a depositable compound may be used without limitation. In addition, when the compound is formed to form a thin film using a coating process, a compound that is dissolved in a solvent and coated may be used without limitation.

Hereinafter, a photoelectric device including the compound according to an embodiment is described with reference to drawings.

FIG. 1 is a cross-sectional view showing a photoelectric device according to an embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and may have a maximum absorption wavelength (Amax) in a wavelength region of about 500 nm to about 600 nm, for example greater than or equal to about 530 nm, greater than or equal to about 535 nm, or greater than or equal to about 540 nm and less than or equal to about 590 nm or less than or equal to about 580 nm.

The active layer 30 may exhibit a light absorption curve having a relatively narrow full width at half maximum (FWHM) of about 50 nm to about 110 nm, for example about 50 nm to about 100 nm. Accordingly, the active layer 30 has high selectivity for light in a green wavelength region.

The active layer may have an absorption coefficient of greater than or equal to about $5.5 \times 10^4$ cm$^{-1}$, for example about $5.8 \times 10^4$ cm$^{-1}$ to about $10 \times 10^4$ cm$^{-1}$, or about $7.0 \times 10^4$ cm$^{-1}$ to about $10 \times 10^4$ cm$^{-1}$ when including the compound Chemical Formula 1 and C60 in a volume ratio of about 0.9:1 to about 1.1:1, for example about 1:1.

The active layer 30 may further include an n-type semiconductor compound for forming a pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, CM, C90, C96, C240, C540, a mixture thereof, a fullerene nanotube, and the like. The fullerene derivative may refer to compounds of these fullerenes having a substituent thereof. The fullerene derivative may include a substituent such as an alkyl group (e.g., C1 to C30 alkyl group), an aryl group (e.g., C6 to C30 aryl group), a heterocyclic group (e.g., C3 to C30 cycloalkyl group), and the like. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathin ring, a phenothiazine ring, or a phenazine ring.

The sub-phthalocyanine or the sub-phthalocyanine derivative may be represented by Chemical Formula 6.

[Chemical Formula 6]

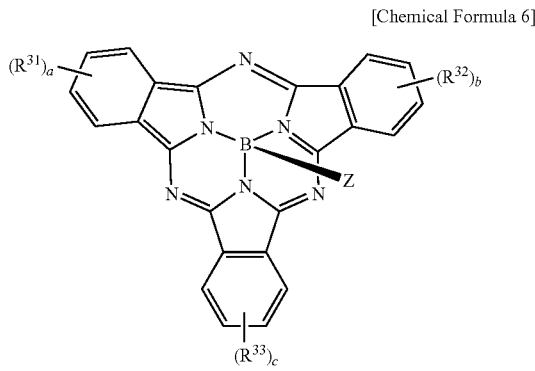

In Chemical Formula 6, $R^{31}$ to $R^{33}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof, a, b, and c are integers ranging from 1 to 3, and Z is a monovalent substituent.

For example, Z may be a halogen or a halogen-containing group, for example F, Cl, an F-containing group, or a Cl-containing group.

The halogen refers to F, Cl, Br, or I and the halogen-containing group refers to alkyl group (C1 to C30 alkyl group) where at least one of hydrogen is replaced by F, Cl, Br, or I.

The thiophene derivative may be for example represented by Chemical Formula 7 or 8, but is not limited thereto.

[Chemical Formula 7]

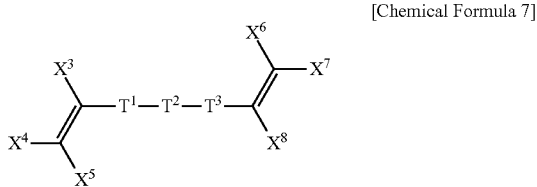

EWG$^1$-T$^1$-T$^2$-T$^3$-EWG$^2$  [Chemical Formula 8]

In Chemical Formulae 7 and 8,

T$^1$, T$^2$, and T$^3$ are aromatic rings including substituted or unsubstituted thiophene moieties, T$^1$, T$^2$, and T$^3$ are each independently present or are fused to each other, $X^3$ to $X^8$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and EWG$^1$ and EWG$^2$ are each independently electron withdrawing groups.

For example, in Chemical Formula 7, at least one of $X^3$ to $X^8$ may be an electron withdrawing group, for example a cyano-containing group.

The active layer 30 may further include a second p-type semiconductor compound selectively absorbing green light. The second p-type semiconductor compound may be a compound represented by Chemical Formula 9.

[Chemical Formula 9]

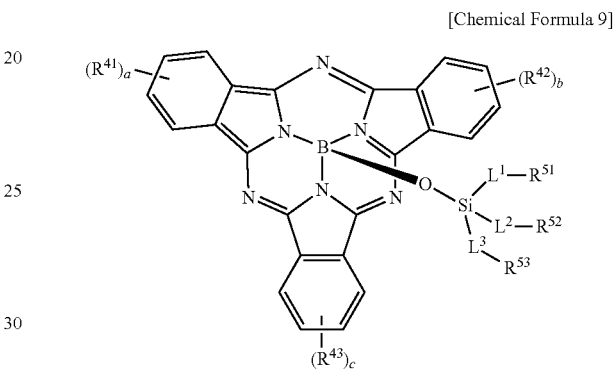

In Chemical Formula 9, $R^{41}$ to $R^{43}$ are each independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, L$^1$ to L$^3$ are each independently a single bond, a substituted or unsubstituted C1 to C30 alkylene group, a substituted or unsubstituted C6 to C30 arylene group, divalent substituted or unsubstituted C3 to C30 heterocyclic group, or a combination thereof, $R^{51}$ to $R^{53}$ are each independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are each independently an integer ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90%.

In the photoelectric device 100, when light enters from the first electrode 10 and/or second electrode 20, and when the active layer 30 absorbs light in a desired and/or alternatively predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another embodiment is described with reference to FIG. 2.

Figure 2:
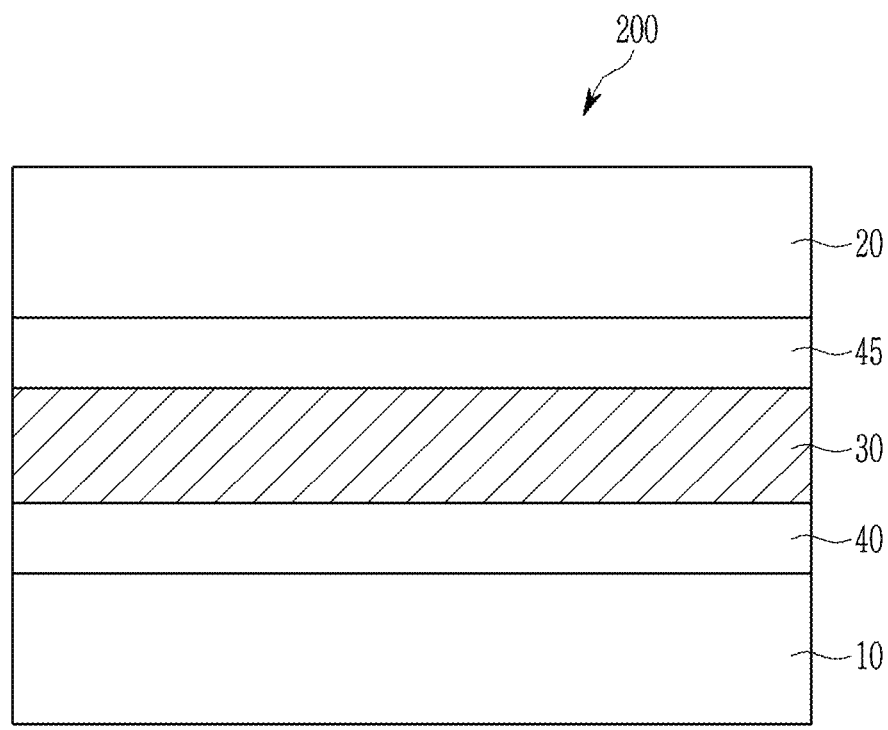
FIG. 2 is a cross-sectional view showing a photoelectric device according to another embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for limiting and/or preventing electron transport, an electron injection layer (EIL) for facilitating electron injection, an electron transport layer (ETL) for facilitating electron transport, and a hole blocking layer (HBL) for limiting and/or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N, N',N'-tetrakis(4-methoxyphenyl)-benzidine (TPD), 4,4'-bis [N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
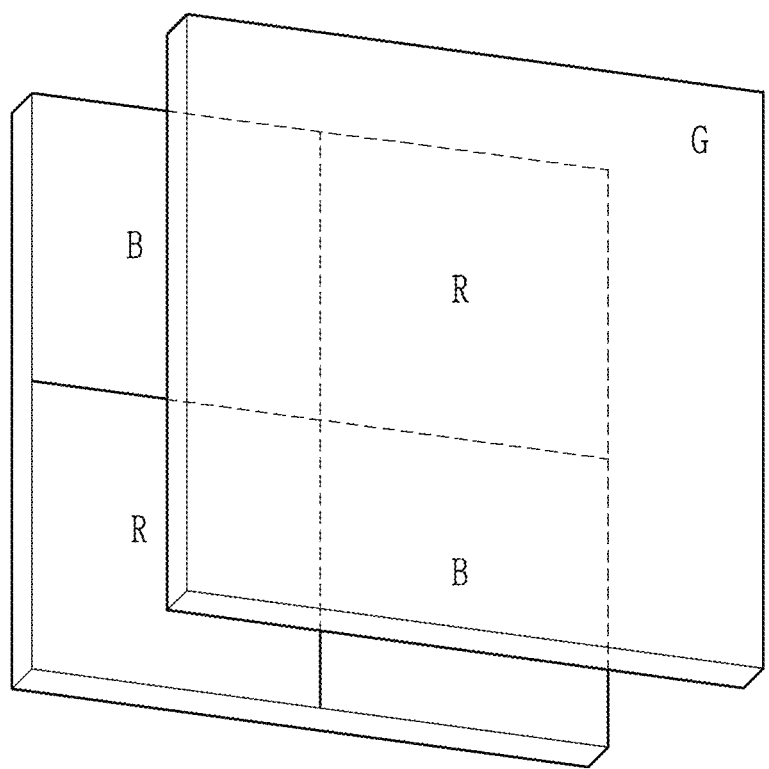
FIG. 3 is a schematic top plan view showing an organic CMOS image sensor according to an embodiment.
Figure 4:
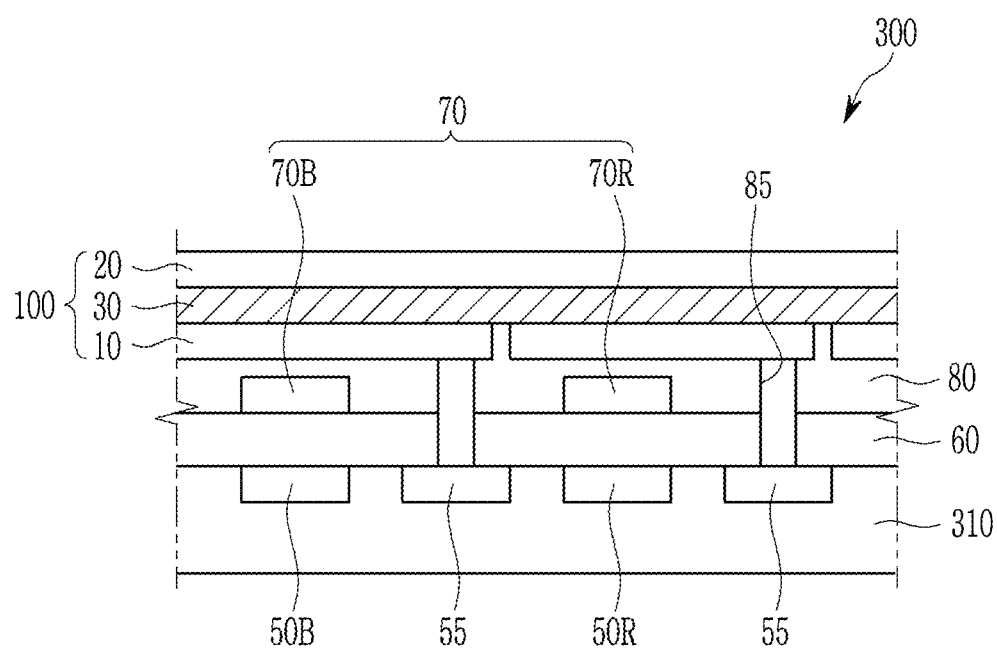
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and a photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In an embodiment, a cyan filter 70C and a yellow filter 70Y may be disposed instead of the blue filter 70B and red filter 70R. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, additional color filters may be further disposed on the photoelectric device 100. The additional color filters may include a blue filter 70B and a red filter 70R or a cyan filter 70C and a yellow filter 70Y.

Figure 5:
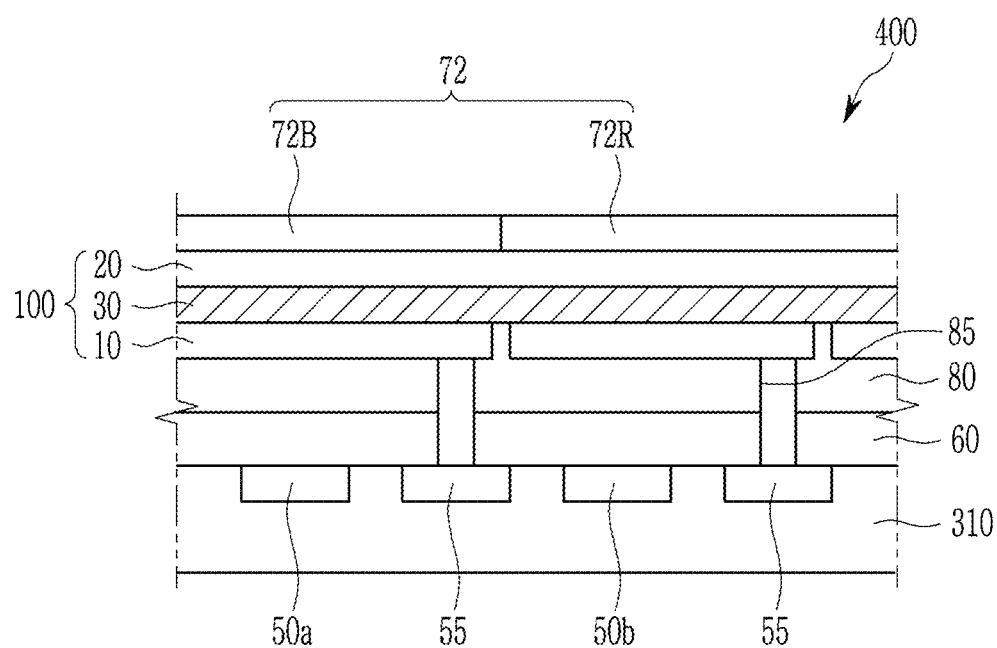
FIG. 5 is a schematic cross-sectional view showing an organic CMOS image sensor according to another embodiment.

The organic CMOS image sensor with the color filters disposed on the photoelectric device is shown in FIG. 5. FIG. 5 is a schematic cross-sectional view showing an organic CMOS image sensor according to an embodiment. Referring to FIG. 5, an organic CMOS image sensor 400 has the same structure as FIG. 4 except that a color filter layer 72 including the blue filter 72B and the red filter 72R is disposed on the photoelectric device 100. Instead of the blue filter 72B and the red filter 72R, the cyan filter 72C and the yellow filter 72Y may be disposed respectively.

Figure 6:
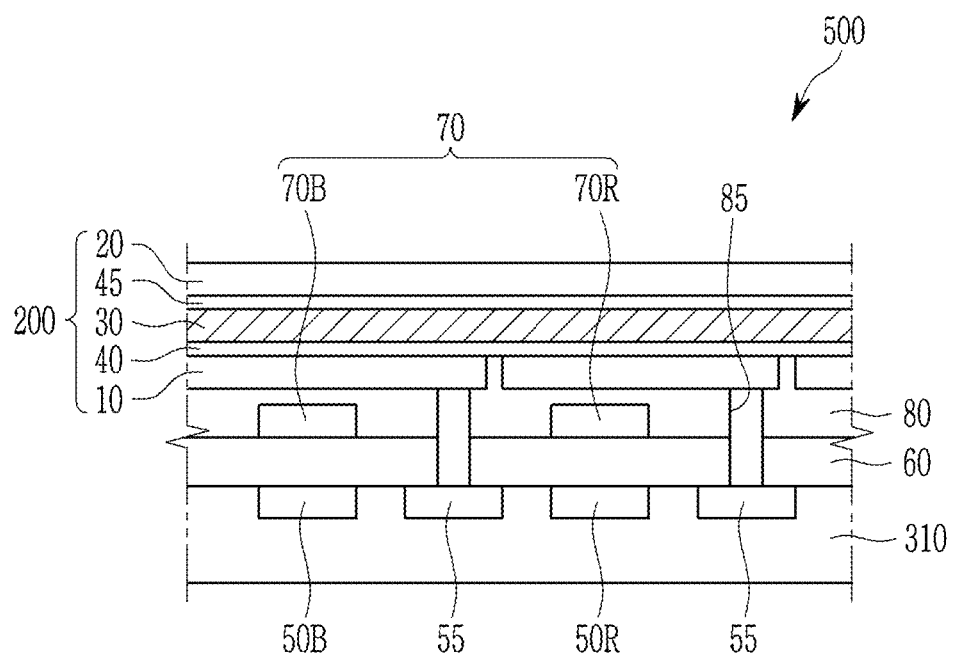
FIG. 6 is a schematic cross-sectional view showing an organic CMOS image sensor according to another embodiment.

In FIGS. 4 and 5, the photoelectric device 100 of FIG. 1 is included, but it is not limited thereto, and thus the photoelectric device 200 of FIG. 2 may be applied in the same manner. FIG. 6 is a cross-sectional view showing an organic CMOS image sensor 500 to which the photoelectric device 200 is applied.

Figure 7:
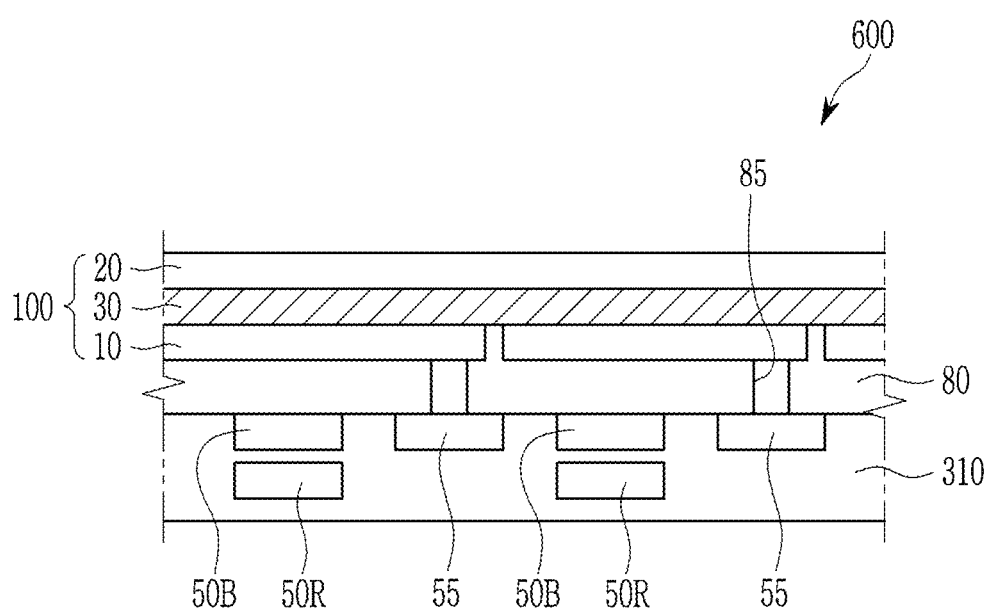
FIG. 7 is a schematic view showing an organic CMOS image sensor according to another embodiment.

FIG. 7 is a schematic view showing an organic CMOS image sensor according to another embodiment.

Referring to FIG. 7, the organic CMOS image sensor 600 includes a semiconductor substrate 310 integrated with photo-sensing devices 50B and 50R, a transmission transistor (not shown), a charge storage 55, an insulation layer 80, and a photoelectric device 100, like the example embodiment illustrated in FIG. 5.

However, the organic CMOS image sensor 600 according to the embodiment includes the blue photo-sensing device 50B and the red photo-sensing device 50R that are stacked and does not include a color filter layer 70, unlike the aforementioned embodiments. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
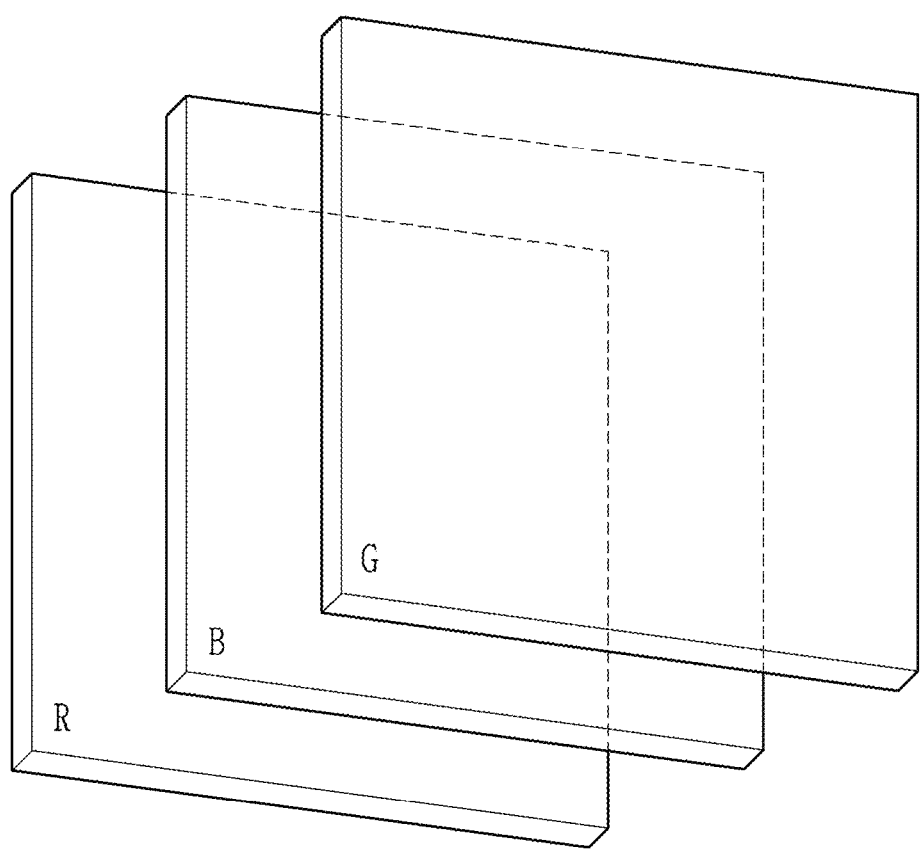
FIG. 8 is a schematic view showing an organic CMOS image sensor according to another embodiment.

FIG. 8 is a schematic view showing an organic CMOS image sensor according to another example embodiment.

Referring to FIG. 8, the organic CMOS image sensor according to the present embodiment includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the aforementioned photoelectric device 100 or photoelectric device 200, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the green photoelectric device (G) selectively absorbing light in a green wavelength region, the blue photoelectric device (B) selectively absorbing light in a red wavelength region, and the red photoelectric device (R) selectively absorbing light in a blue wavelength region are stacked, and thereby a size of an image sensor may be decreased and a down-sized image sensor may be realized.

The image sensor absorbs light in an appropriate wavelength region and may show all improved sensitivity (YSNR10) and color reproducibility (ΔE*ab) despite a stack structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Maine, USA) but minimum illuminance expressed by lux at a ratio of 10 between signal and noise. Accordingly, the smaller the YSNR10 is, the higher sensitivity is.

On the other hand, the color reproducibility (ΔE*ab) shows a difference from standard colors in an X-Rite chart, and the ΔE*ab is defined as a distance between two points on a L*a*b* color space by CIE (Commission International de L'Eclairage) in 1976. For example, the color difference may be calculated according to Equation 1.

$$\Delta E = \sqrt{(\Delta L^*)^2 + (\Delta a^*)^2 + (\Delta b^*)^2}$$ [Equation 1]

In Equation 1,

ΔL* denotes a change of a color coordinate L* compared with the color coordinate L* at room temperature (about 20° C. to about 25° C.), Δa* denotes a change of a color coordinate a* compared with the color coordinate a* at room temperature, and Δb* denotes a change of a color coordinate b* compared with the color coordinate b* at room temperature.

In order to manufacture an image sensor having high sensitivity and high color reproducibility, YSNR10≤100 lux at ΔE*ab≤3, and herein, the compound may realize YSNR10≤100 lux of sensitivity and color reproducibility at ΔE*ab≤3.

The image sensor may be applied to various electronic devices, for example, a mobile phone, a digital camera, and the like but is not limited thereto.

Figure 9:
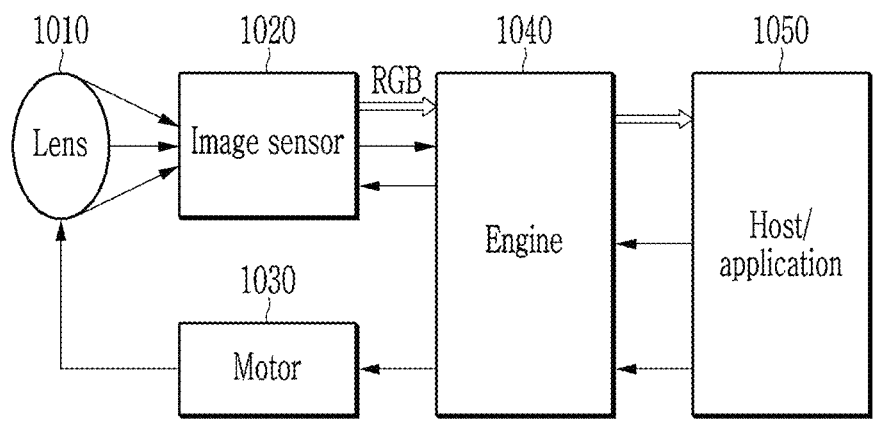
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor 1030, and an engine 1040. The image sensor 1020 may be one of image sensors according to embodiments shown in FIGS. 3 to 8.

The lens 1010 concentrates incident light on the image sensor 1020. The image sensor 1020 generates RGB data for received light through the lens 1010.

In some embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

In example embodiments, the motor 1030, engine 1040, and host/application 1050 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

Hereinafter, the embodiments are illustrated in more detail with reference to examples. However, these examples are non-limiting, and inventive concepts are not limited thereto.

Synthesis Example 1: Synthesis of Compound Represented by Chemical

Formula 1-1 (2-((5-(10H-phenotellurazin-10-yl)tellurophen-2-yl)methylene)-1H-indene-1,3(2H)-dione)

[Chemical Formula 1-1]

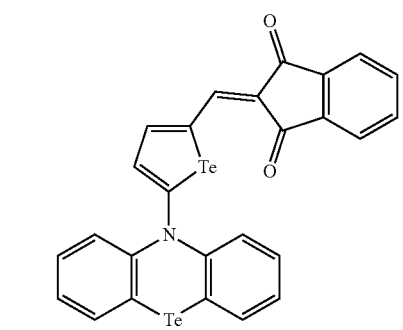

[Reaction Scheme 1-1]

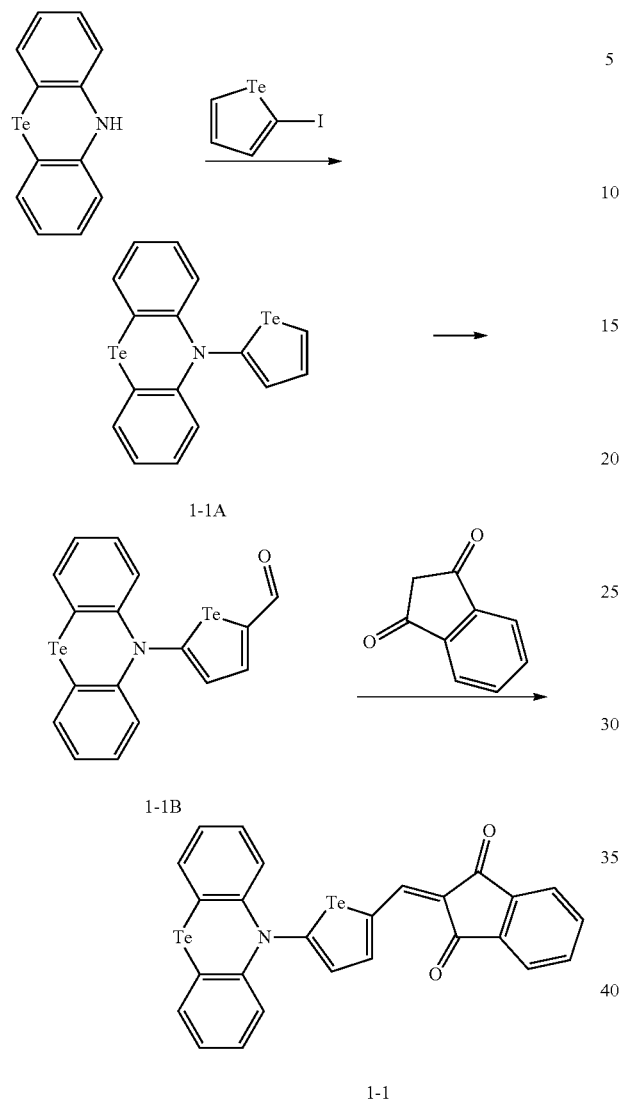

(i) Synthesis of Compound 1-1A 13.2 g (43.2 mmol) of 2-iodotellurophene and 10.6 g (35.6 mmol) of 10H-phenotellurzine are heated and refluxed in 150 ml of anhydrous toluene under 5 mol % of Pd(dba)$_2$, 5 mol % of P(tBu)$_3$, and 10.4 g (107.9 mmol) of NaOtBu for 2 hours. A product obtained therefrom is separated and purified through silica gel column chromatography (hexane:ethylacetate=volume ratio of 4:1) to obtain 8.35 g of 10-(tellurophen-2-yl)-10H-phenotellurazine (Yield: 49.8%).

(ii) Synthesis of Compound 1-1B 1.28 ml (13.8 mmol) of phosphoryl chloride is added in a dropwise fashion to 4.1 ml (53.0 mmol) of N,N-dimethyl-formamide at −15° C., and the mixture is stirred at room temperature for 2 hours. The resultant therefrom is slowly added in a dropwise fashion to a mixture of 200 ml of dichloromethane and 5.0 g (10.6 mmol) of Compound 1-1A at −15° C. and the mixture is stirred at room temperature for 2 hours. 100 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 5.00 g of 5-(10H-phenotellurazin-10-yl)tellurophene-2-carbaldehyde (Yield: 94.0%).

(iii) Synthesis of Compound Represented by Chemical Formula 1-1

1.20 g (2.4 mmol) of Compound 1-1B is suspended in ethanol, 0.42 g (2.9 mmol) of 1H-indene-1,3(2H)-dione, and then the mixture is heated and refluxed at 50° C. for 2 hours. After cooling the resultant to room temperature, hexane is added. When powder is formed, the powder is filtered, and the resultant is separated and purified through by silica gel column chromatography (dichloromethane) to obtain 1.3 g of Compound 1-1 (Yield: 87.0%). The obtained Compound 1-1 is sublimed and purified up to purity of 99.9%.

$^1$H-NMR (500 MHz, Methylene Chloride-d2): δ 8.20 (d, 1H), 7.88 (s, 1H), 7.81 (d, 2H), 7.75-7.63 (m, 4H), 7.55 (d, 2H), 7.47 (t, 2H), 7.36 (t, 2H), 6.97 (d, 1H).

Synthesis Example 2: Synthesis of Compound Represented by Chemical Formula 1-2 (5-((5-(10H-phenotellurazin-10-yl)tellurophen-2-yl)methylene)-1,3-dimethyl-2-thioxodihydropyrimidine-4,6(1H, 5H)-dione)

[Chemical Formula 1-2]

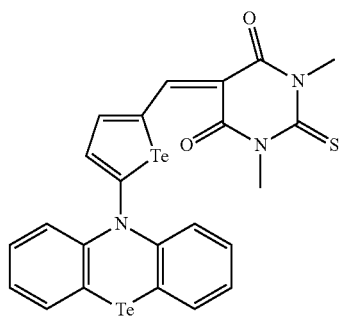

[Reaction Scheme 1-2]

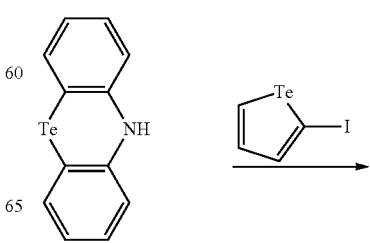

-continued

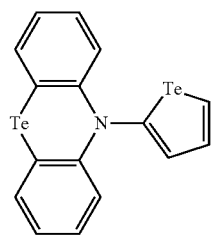

1-1A

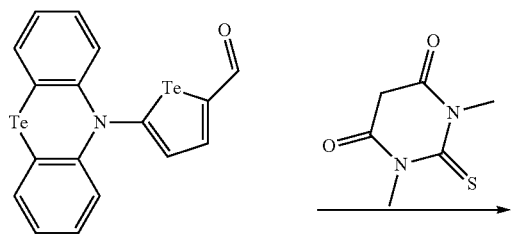

1-1B

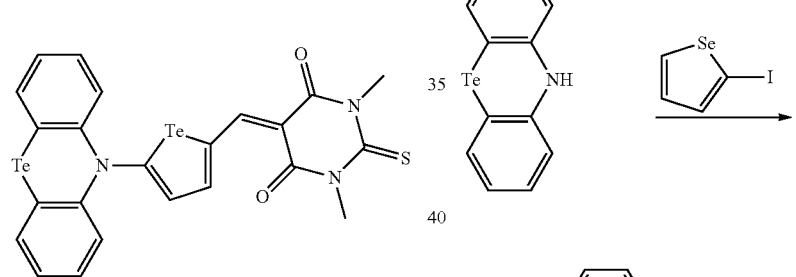

1-2

(i) Synthesis of Compound Represented by Chemical Formula 1-2

1.20 g (2.4 mmol) of Compound 1-1B obtained in the (ii) step of Synthesis Example 1 is suspended in ethanol, 0.493 g (2.9 mmol) of 1,3-dimethyl-2-thioxodihydropyrimidine-4,6(1H,5H)-dione is added thereto, and then, the mixture is heated and refluxed at 50° C. for 2 hours. After cooling the resultant to room temperature, hexane is added. When powder is formed, the powder is filtered, and the resultant is separated and purified through by silica gel column chromatography (dichloromethane) to obtain 1.3 g of Compound 1-2 (Yield: 87.0%)

The obtained Compound 1-2 is sublimed and purified up to purity of 99.9%.

$^1$H-NMR (500 MHz, Methylene Chloride-d2): δ 8.50 (s, 1H), 8.32 (d, 1H), 7.81 (d, 2H), 7.56 (d, 2H), 7.48 (t, 2H), 7.36 (t, 2H), 7.13 (d, 2H), 3.7 (d, 6H).

Synthesis Example 3: Synthesis of Compound Represented by Chemical Formula 1-3 (2-((5-(10H-phenotellurazin-10-yl)selenophen-2-yl)methylene)-1H-indene-1,3(2H)-dione)

[Chemical Formula 1-3]

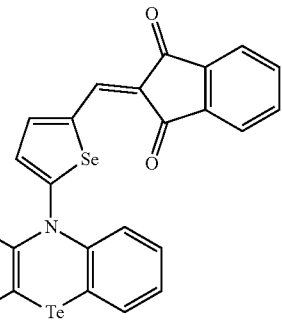

[Reaction Scheme 1-3]

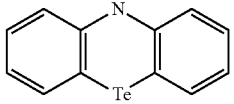

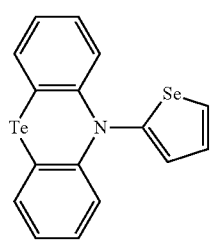

1-3A

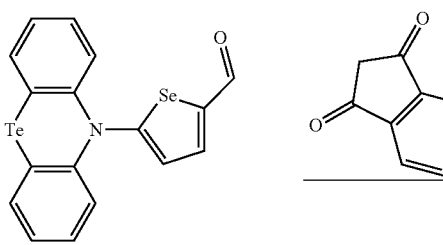

1-3B

-continued

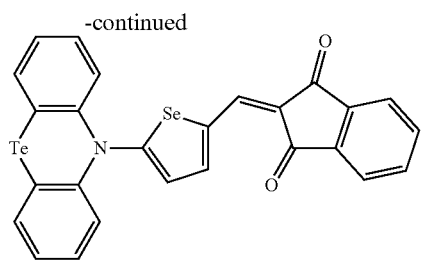

1-3

(i) Synthesis of Compound 1-3A 11.1 g (43.2 mmol) of 2-iodoselenophene and 10.6 g (35.6 mmol) of 10H-phenotellurzine are heated and refluxed in 150 ml of anhydrous toluene under 5 mol % of Pd(dba)$_2$, 5 mol % of P(tBu)$_3$, and 10.4 g (107.9 mmol) of NaOtBu for 2 hours. A product obtained therefrom is separated and purified through silica gel column chromatography (hexane: ethylacetate=volume ratio of 4:1) to obtain 8.1 g of 10-(selenophen-2-yl)-10H-phenotellurazine (Yield: 47.6%).

(ii) Synthesis of Compound 1-3B 1.4 ml (14.3 mmol) of phosphoryl chloride is added in a dropwise fashion to 4.3 ml (55.0 mmol) of N, N-dimethyl-formamide at −15° C., and the mixture is stirred at room temperature (24° C.) for 2 hours. The resultant therefrom is slowly added in a dropwise fashion to a mixture of 200 ml of dichloromethane and 4.7 g (11.0 mmol) of Compound 1-3A at −15° C. and the mixture is stirred at room temperature for 2 hours. 100 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 4.5 g of Compound 1-3B (5-(10H-phenotellurazin-10-yl)selenophene-2-carbaldehyde) (Yield: 90.0%).

(iii) Synthesis of Compound Represented by Chemical Formula 1-3

1.20 g (2.6 mmol) of the obtained Compound 1-3B is suspended in ethanol, 0.45 g (3.1 mmol) of 1H-indene-1,3 (2H)-dione is added thereto, and then, the mixture is heated and refluxed at 50° C. for 2 hours. After cooling the resultant to room temperature, hexane is added. When powder is formed, the powder is filtered, and the resultant is separated and purified through by silica gel column chromatography (dichloromethane) to obtain 1.3 g of Compound 1-3 (Yield: 87.0%). The obtained Compound 1-3 is sublimed and purified up to purity of 99.9%.

$^1$H-NMR (500 MHz, Methylene Chloride-d2): δ 7.88 (s, 1H) 7.86 (d, 1H), 7.81 (d, 2H), 7.75-7.63 (m, 4H), 7.55 (d, 2H), 7.47 (t, 2H), 7.36 (t, 2H), 6.67 (d, 1H).

Synthesis Example 4: Synthesis of Compound Represented by Chemical Formula 1-4 (5-((5-(10H-phenotellurazin-10-yl)selenophen-2-yl)methylene)-1,3-dimethyl-2-thioxodihydropyrimidine-4,6(1H, 5H)-dione)

[Chemical Formula 1-4]

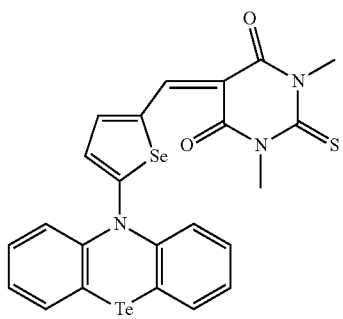

[Reaction Scheme 1-4]

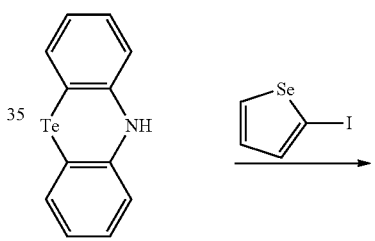

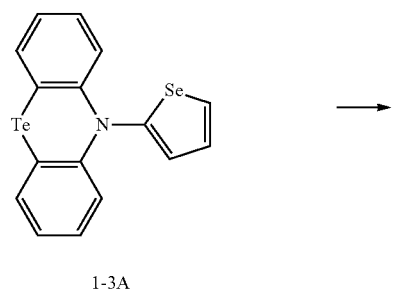

1-3A

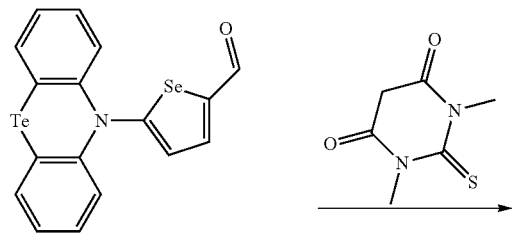

1-3B

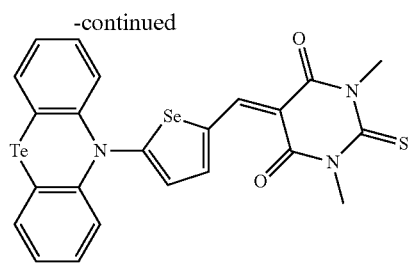

1-4

(i) Synthesis of Compound Represented by Chemical Formula 1-4

1.18 g (2.5 mmol) of Compound 1-3B obtained in the (ii) step of Synthesis Example 3 is suspended in ethanol, 0.511 g (3.0 mmol) of 1,3-dimethyl-2-thioxodihydropyrimidine-4,6(1H,5H)-dione is added thereto, and then, the mixture is heated and refluxed at 50° C. for 2 hours. After cooling the resultant to room temperature, hexane is added. When powder is formed, the powder is filtered, and the resultant is separated and purified through by silica gel column chromatography (dichloromethane) to obtain 1.25 g of Compound 1-4 (Yield: 83.0%). The obtained Compound 1-4 is sublimed and purified up to purity of 99.9%.

$^1$H-NMR (500 MHz, Methylene Chloride-d2): δ 8.50 (s, 1H), 8.29 (d, 1H), 7.81 (d, 2H), 7.56 (d, 2H), 7.48 (t, 2H), 7.36 (t, 2H), 6.81 (d, 2H), 3.7 (d, 6H).

Reference Synthesis Example 1: Synthesis of Compound Represented by Chemical Formula 2-1 (2-((5-(10H-phenoselenazin-10-yl)tellurophen-2-yl)methylene)-1H-indene-1,3(2H)-dione)

[Chemical Formula 2-1]

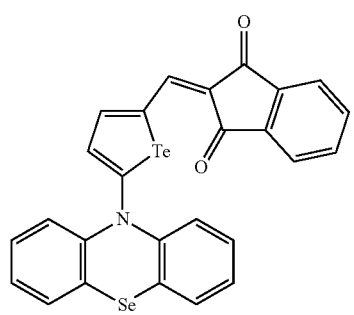

[Reaction Scheme 2-1]

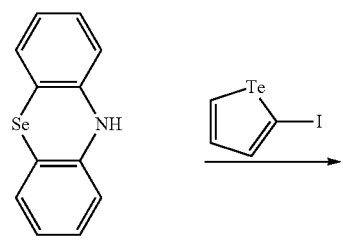

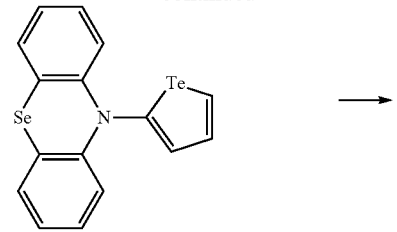

2-1A

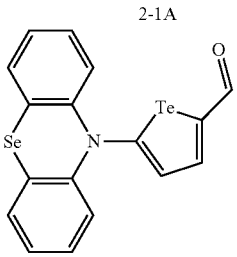 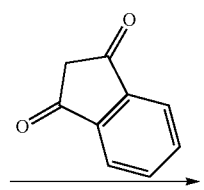

2-1B

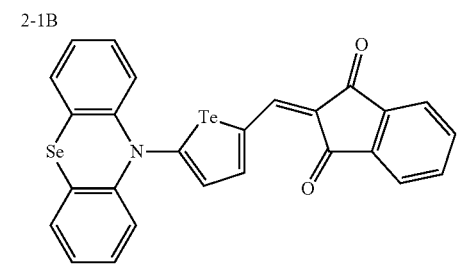

2-1

(i) Synthesis of Compound 2-1A 10.0 g (32.7 mmol) of 2-iodotellurophene and 6.17 g (25.2 mmol) of 10H-phenoselenazine are heated and refluxed in 100 ml of anhydrous toluene under 5 mol % of Pd(dba)$_2$, 5 mol % of P(tBu)$_3$, and 2.66 g (27.7 mmol) of NaOtBu for 2 hours. A product therefrom is separated and purified through silica gel column chromatography (toluene:hexane=volume ratio of 1:4) to obtain 4.25 g of 10-(tellurophen-2-yl)-10H-phenoselenazine (Yield: 39.8%).

(ii) Synthesis of Compound 2-1B 1.84 ml of phosphoryl chloride is added in a dropwise fashion to 6.0 ml of N,N-dimethylformamide at −15° C., and the mixture is stirred at room temperature for 2 hours. The resultant therefrom is slowly added in a dropwise fashion to a mixture of 200 ml of dichloromethane and 4.25 g of Compound 2-1A at −15° C. and the mixture is stirred at room temperature for 30 minutes and concentrated under a reduced pressure. 100 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 2.50 g of 5-(10H-phenoselenazin-10-yl)tellurophene-2-carbaldehyde (Yield: 55.2%).

(iii) Synthesis of Compound Represented by Chemical Formula 2-1

2.50 g (4.21 mmol) of the obtained Compound 2-1B is suspended in ethanol, 0.74 g (5.05 mmol) of 1H-Indene-1,3(2H)-dione is added thereto, and then, the mixture is reacted at 50° C. for 2 hours to obtain 2.02 g of the compound represented by Chemical Formula 2-1 (Yield: 82.8%). The compound is sublimed and purified up to purity of 99.9%.

$^1$H-NMR (500 MHz, Methylene Chloride-d2): δ 7.87 (s, 1H), 7.72 (m, 6H), 7.49 (m, 4H), 7.34 (m, 3H), 6.82 (d, 1H).

[Reaction Scheme 2-2]

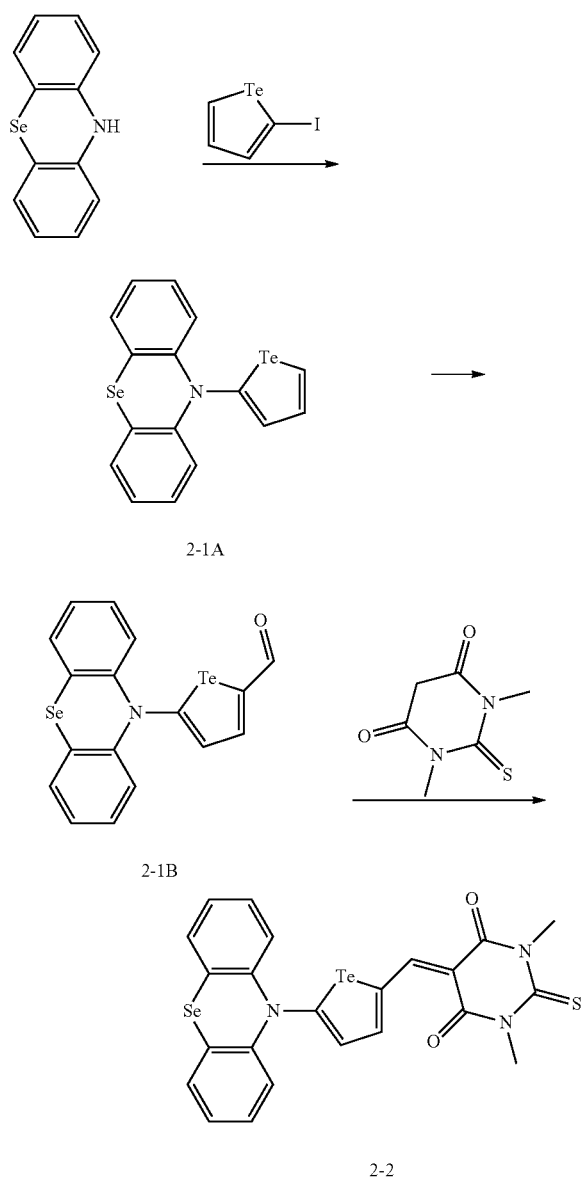

2-1A 2-1B 2-2

Reference Synthesis Example 2: Synthesis of Compound Represented by Chemical Formula 2-2 (5-((5-(10H-phenoselenazin-10-yl)tellurophen-2-yl)methylene)-1,3-dimethyl-2-thioxodihydropyrimidine-4,6(1H,5H)-dione)

[Chemical Formula 2-2]

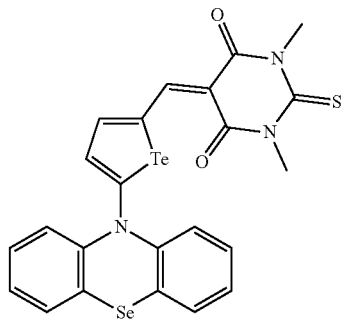

(i) Synthesis of Compound 2-1A 10.0 g (32.7 mmol) of 2-iodotellurophene and 6.17 g (25.2 mmol) of 10H-phenoselenazine are heated and refluxed in 100 ml of anhydrous toluene under 5 mol % of Pd(dba)$_2$, 5 mol % of P(tBu)$_3$, and 2.66 g (27.7 mmol) of NaOtBu for 2 hours. A product therefrom is separated and purified through silica gel column chromatography (toluene:hexane=volume ratio of 1:4) to obtain 4.25 g of 10-(tellurophen-2-yl)-10H-phenoselenazine (Yield: 19.6%).

(ii) Synthesis of Compound 2-1B 1.84 ml of phosphoryl chloride is added in a dropwise fashion to 6.0 ml of N,N-dimethylformamide at −15° C., and the mixture is stirred at room temperature for 2 hours. The resultant therefrom is slowly added in a dropwise fashion to a mixture of 180 ml of dichloromethane and 2.10 g of Compound 2-1A at −15° C., and the obtained mixture is stirred at room temperature for 30 minutes and concentrated under a reduced pressure. Subsequently, 100 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product therefrom is separated and purified through silica gel column chromatography (hexane:ethylacetate=volume ratio of 4:1) to obtain 2.50 g of 5-(10H-phenoselenazin-10-yl)tellurophene-2-carbaldehyde (Yield: 53.6%).

(iii) Synthesis of Compound Represented by Chemical Formula 2-2

2.50 g (4.21 mmol) of the obtained Compound 2-1B is suspended in ethanol, 0.87 g (5.05 mmol) of 1H-Indene-1,3(2H)-dione is added thereto, and then the mixture is reacted at 50° C. for 2 hours to obtain 2.02 g of the final compound represented by Chemical Formula 2-1 (Yield: 82.8%). The compound is sublimed and purified up to purity of 99.9%.

$^1$H-NMR (500 MHz, Methylene Chloride-d$_2$): δ 8.29 (s, 1H), 7.83 (d, 1H), 7.73 (d, 2H), 7.51 (d, 2H), 7.37 (t, 2H), 6.99 (t, 2H), 5.32 (d, 1H), 3.67 (d, 6H).

Reference Synthesis Example 3: Synthesis of Compound Represented by Chemical Formula 2-3

[Chemical Formula 2-3]

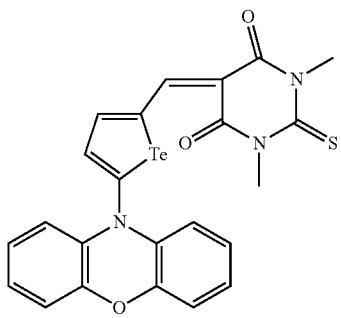

[Reaction Scheme 2-3]

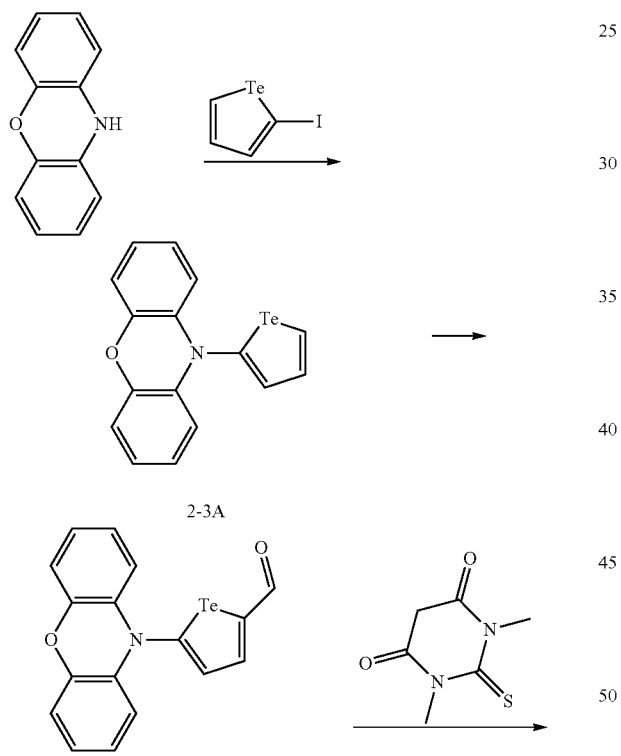

(i) Synthesis of Compound 2-3A 15.2 g (49.9 mmol) of 2-iodotellurophene and 7.6 g (41.6 mmol) of 10H-phenoxazine are heated and refluxed in 150 ml of anhydrous toluene under 5 mol % of Pd(dba)$_2$, 5 mol % of P(tBu)$_3$, and 10.4 g (107.9 mmol) of NaOtBu for 2 hours. A product therefrom is separated and purified through silica gel column chromatography (toluene:hexane=volume ratio of 1:4) to obtain 9.1 g of 10-(tellurophen-2-yl)-10H-phenoxazine (Yield: 61.0%).

(ii) Synthesis of Compound 2-3B 1.25 ml (13.4 mmol) of phosphoryl chloride is added in a dropwise fashion to 4.0 ml (51.4 mmol) of N,N-dimethylformamide, and the mixture is stirred at room temperature for 2 hours. The resultant therefrom is slowly added in a dropwise fashion to a mixture of 200 ml of dichloromethane and 3.7 g (10.6 mmol) of Compound 2-3A at −15° C. and the mixture is stirred at room temperature for 2 hours. 100 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 3.5 g of 5-(10H-phenoxazin-10-yl)tellurophene-2-carbaldehyde (Yield: 88.0%).

(iii) Synthesis of Compound Represented by Chemical Formula 2-3

1.18 g (3.0 mmol) of the obtained Compound 2-3B is suspended in ethanol, 0.63 g (3.6 mmol) of 1,3-dimethyl-2-thioxodihydropyrimidine-4,6(1H,5H)-dione is added thereto, and then, the mixture is heated and refluxed at 50° C. for 2 hours. After cooling the resultant to room temperature, hexane is added. When powder is formed, the powder is filtered, and the resultant is separated and purified through by silica gel column chromatography (dichloromethane) to obtain 1.25 g of Compound 2-3 (Yield: 83.0%). The compound is sublimed and purified up to purity of 99.9%.

$^1$H-NMR (500 MHz, Methylene Chloride-d2): δ 8.50 (s, 1H), 8.31 (d, 1H), 7.81 (d, 2H), 7.48 (t, 2H), 7.43-7.36 (m, 4H), 7.06 (d, 1H), 3.7 (d, 6H).

Reference Synthesis Example 4: Synthesis of Compound Represented by Chemical Formula 2-4

[Chemical Formula 2-4]

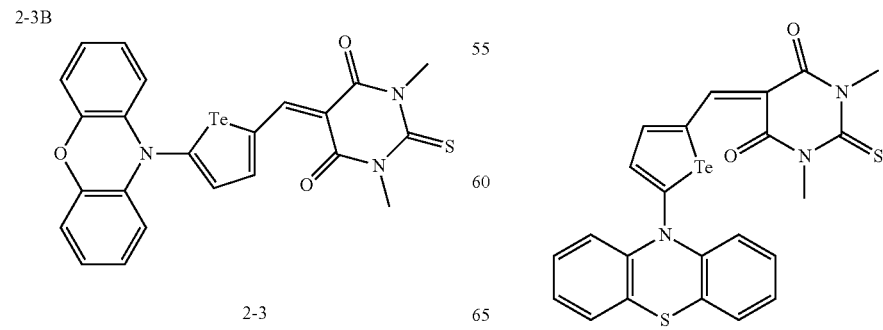

[Reaction Scheme 2-4]

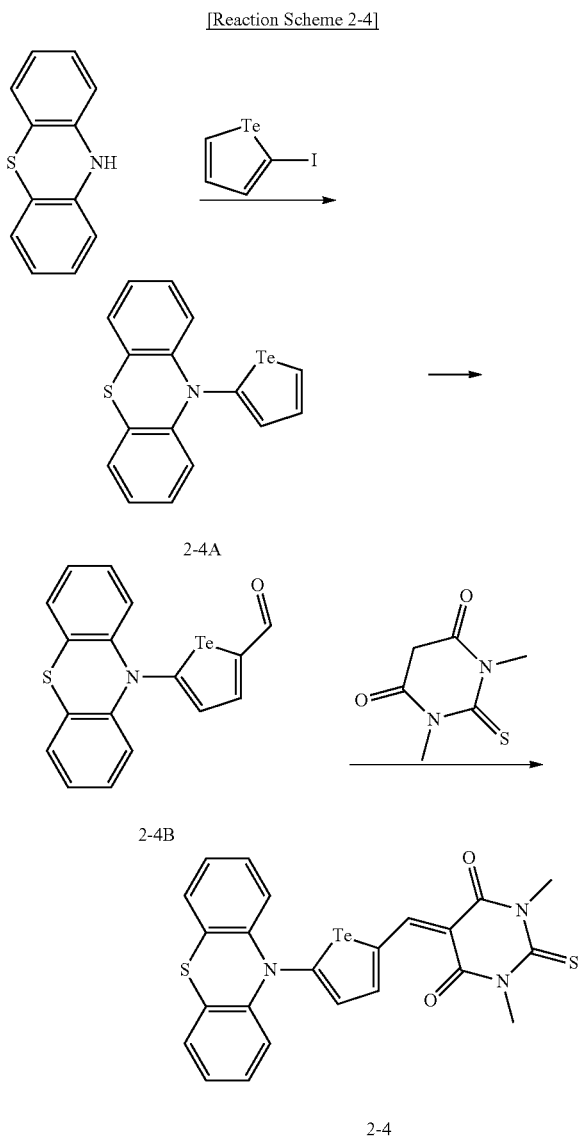

11.7 g (38.2 mmol) of 2-iodotellurophene and 6.3 g (31.8 mmol) of 10H-phenothiazine are heated and refluxed in 150 ml of anhydrous toluene under 5 mol % of Pd(dba)$_2$, 5 mol % of P(tBu)$_3$, and 9.2 g (95.5 mmol) of NaOtBu for 2 hours. A product therefrom is separated and purified through silica gel column chromatography (toluene:hexane=volume ratio of 1:4) to obtain 7.0 g of 10-(tellurophen-2-yl)-10H-phenothiazine (Yield: 58.0%).

(ii) Synthesis of Compound 2-4B 1.6 ml (17.6 mmol) of phosphoryl chloride is added in a dropwise fashion to 5.3 ml (67.9 mmol) of N,N-dimethylformamide at −15° C., and the mixture is stirred at room temperature for 2 hours. The resultant therefrom is slowly added in a dropwise fashion to a mixture of 200 ml of dichloromethane and 5.1 g (13.6 mmol) of Compound 2-4A and the mixture is stirred at room temperature for 2 hours. 100 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 3.5 g of 5-(10H-phenoxazin-10-yl)tellurophene-2-carbaldehyde (Yield: 88.0%).

(iii) Synthesis of Compound Represented by Chemical Formula 2-4

1.09 g (2.7 mmol) of the obtained Compound 2-4B is suspended in ethanol, 0.55 g (3.2 mmol) of 1,3-dimethyl-2-thioxodihydropyrimidine-4,6(1H,5H)-dione is added thereto, and then, the mixture is heated and refluxed at 50° C. for 2 hours. After cooling the resultant to room temperature, hexane is added. When powder is formed, the powder is filtered, and the resultant is separated and purified through by silica gel column chromatography (dichloromethane) to obtain 1.30 g of Compound 2-4 (Yield: 87.0%). The compound is sublimed and purified up to purity of 99.9%.

$^1$H-NMR (500 MHz, Methylene Chloride-d2): δ 8.50 (s, 1H), 8.31 (d, 1H), 7.81 (d, 2H), 7.48 (t, 2H), 7.55 (d, 2H), 7.36 (d, 2H), 7.04 (1, 2H), 3.7 (d, 6H).

Reference Synthesis Example 5: Synthesis of Compound Represented by Chemical Formula 2-5

[Chemical Formula 2-5]

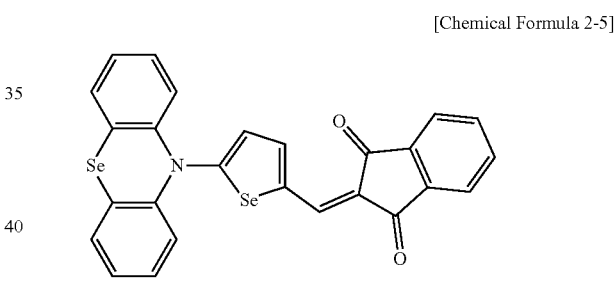

[Reaction Scheme 2-5]

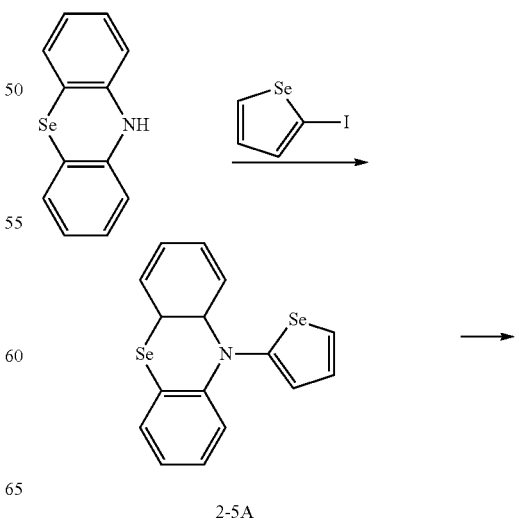

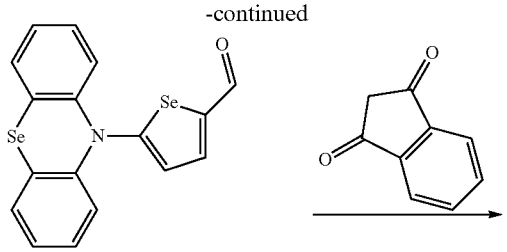

2-5B

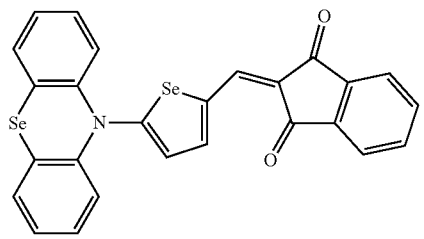

2-5

(i) Synthesis of Compound 2-5A 12.32 g (47.98 mmol) of 2-iodoselenophene and 9.84 g (39.98 mmol) of 10H-phenoselenazine are heated and refluxed in 100 ml of anhydrous toluene under 5 mol % of Pd(dba)$_2$, 5 mol % of P(tBu)$_3$, and 10.2 g (119.94 mmol) for 2 hours. A product therefrom is separated and purified through silica gel column chromatography (toluene:hexane=volume ratio of 1:4) to obtain 10.0 g of 10-(selenophen-2-yl)-10H-phenoselenazine (Yield: 67.2%).

(ii) Synthesis of Compound 2-5B 1.65 ml (17.7 mmol) of phosphoryl chloride is added in a dropwise fashion to 5.28 ml (68.2 mmol) of N,N-dimethylformamide at −15° C., and the mixture is stirred at room temperature for 2 hours. The resultant therefrom is slowly added in a dropwise fashion to a mixture of 200 ml of dichloromethane and 5.12 g (13.6 mmol) of Compound 2-5A at −15° C. and the mixture is stirred at room temperature for 30 minutes and concentrated under a reduced pressure. 200 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 5.0 g of 5-(10H-phenoselenazin-10-yl) selenophene-2-carbaldehyde (Yield: 91.1%).

(iii) Synthesis of Compound Represented by Chemical Formula 2-5

1.14 g (2.82 mmol) of the obtained Compound 2-5B is suspended in ethanol, 0.58 g (3.39 mmol) of 1H-Indene-1,3(2H)-dione is added thereto, and then, the mixture is reacted at 50° C. for 2 hours to obtain 1.17 g of the compound represented by Chemical Formula 2-5 (Yield: 78.1%). The compound is sublimed and purified up to purity of 99.9%.

$^1$H-NMR (500 MHz, Methylene Chloride-d$_2$): δ 7.87 (s, 1H), 7.72 (m, 6H), 7.49 (m, 4H), 7.42 (m, 3H), 6.82 (d, 1H).

Reference Synthesis Example 6: Synthesis of Compound Represented by Chemical Formula 2-6

[Chemical Formula 2-6]

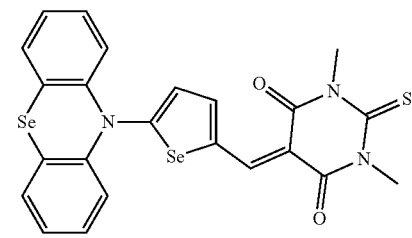

[Reaction Scheme 2-6]

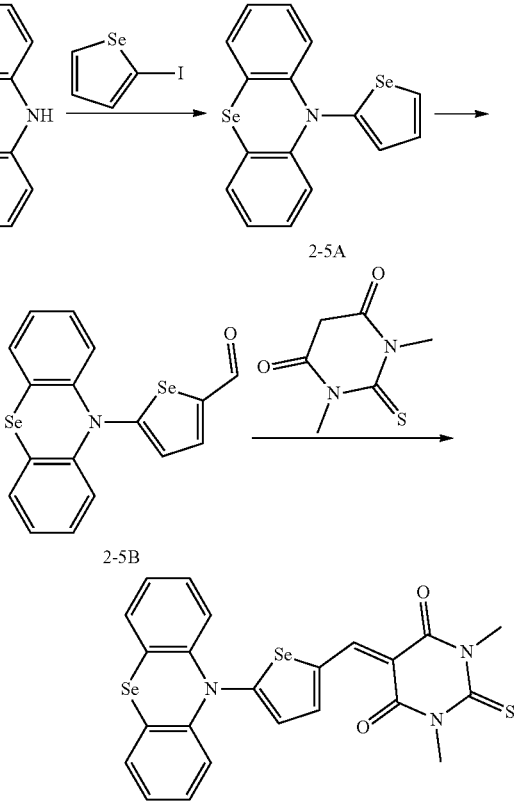

(i) Synthesis of Compound Represented by Chemical Formula 2-6

2.00 g (4.96 mmol) of Compound 2-5B obtained in the (ii) step of Reference Synthesis Example 5 is suspended in ethanol, 1.03 g (5.95 mmol) of 1,3-dimethyl-2-thiobarbituric acid is added thereto, and then, the mixture is heated and refluxed at 50° C. for 2 hours to obtain 2.15 g of the compound represented by Chemical Formula 2-6 (Yield: 77.8%). The compound is sublimed and purified up to purity of 99.9%.

¹H-NMR (500 MHz, Methylene Chloride-d₂): δ 8.29 (s, 1H), 7.83 (d, 1H), 7.73 (d, 2H), 7.51 (d, 2H), 7.37 (t, 2H), 7.16 (t, 2H), 5.32 (d, 1H), 3.67 (d, 6H).

Reference Synthesis Example 7: Synthesis of Compound Represented by Chemical Formula 2-7

[Chemical Formula 2-7]

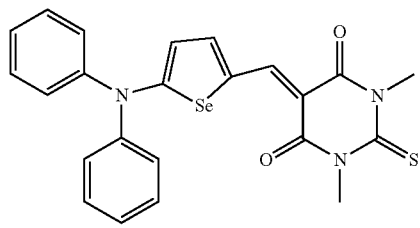

(i) Synthesis of Compound 2-7A

[Reaction Scheme 2-7]

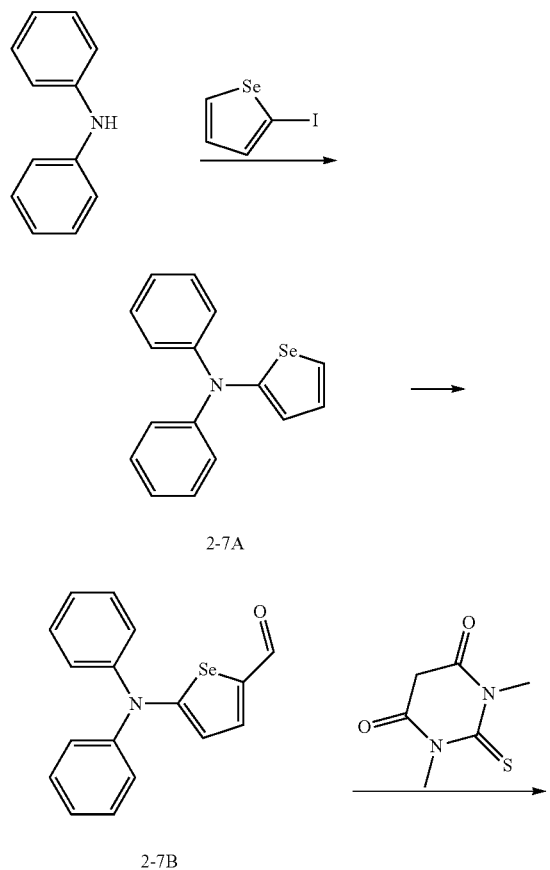

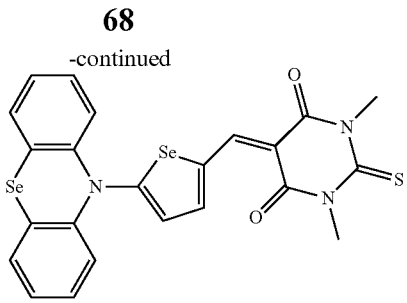

2-7

2.0 g (7.80 mmol) of 2-iodoselenophene (Compound 1) and 1.2 g (7.09 mmol) of diphenylamine are heated and refluxed in 30 ml of anhydrous toluene under 5 mol % of Pd(dba)₂, 5 mol % of P(tBu)₃, and 0.75 g (7.80 mmol) of NaOtBu for 2 hours. A product obtained therefrom is separated and purified through silica gel column chromatography (hexane:hexane=volume ratio of 1:4) to obtain 1.40 g of Compound 2-7A (Yield: 66.2%).

(ii) Synthesis of Compound 2-7B 1.75 ml of phosphoryl chloride is added in a dropwise fashion to 6.0 ml of N,N-dimethylformamide at −15° C., and the mixture is stirred at room temperature for 2 hours. The resultant therefrom is slowly added in a dropwise fashion to a mixture of 60 ml of dichloromethane and 1.4 g of Compound 2-7A at −15° C. and the mixture is stirred at room temperature for 30 minutes and concentrated under a reduced pressure. 100 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 1.0 g of Compound 2-7B (Yield: 65.3%).

(iii) Synthesis of Compound Represented by Chemical Formula 2-7

0.33 g (1.09 mmol) of the obtained Compound 2-7B is suspended in ethanol, 0.23 g (1.3 mmol) of 1,3-dimethyl-2-thiobarbituric acid is added thereto, and then, the mixture is heated and refluxed at 50° C. for 2 hours to obtain 0.47 g of the compound represented by Chemical Formula 2-7 (Yield: 90%).

¹H-NMR (500 MHz, Methylene Chloride-d2): 8.5 (s, 1H), 7.9 (d, 1H), 7.5-7.3 (m, 10H), 6.6 (d, 1H), 3.7 (d, 6H)

Evaluation 1: Light Absorption Characteristics of Compounds of Synthesis Examples 1 to 4

Light absorption characteristics (maximum absorption wavelength, full width at half maximum (FWHM), and absorption coefficient) and energy levels of the compounds according to Synthesis Examples 1 to 4 are evaluated. Each compound according to Synthesis Examples 1 to 4 and C60 are codeposited in a volume ratio of 1:1 to provide each thin film. Light absorption characteristics of each film are evaluated by using an ultraviolet (UV)-visible ray (UV-Vis) with Cary 5000 UV Spectroscopy (Varian Medical Systems). In addition, an AC-3 photoelectron spectrophotometer (RIKEN KEIKI) is used to measure HOMO energy level, and a bandgap is measured by using Cary 5000 UV spectroscopy (Varian Medical Systems, Inc.) and then, used to calculate LUMO energy level. The results are shown in Table 1.

Referring to Table 1, maximum absorption wavelengths of the compounds according to Synthesis Examples 1 to 4 are in a green wavelength region, full widths at half maximum (FWHM) thereof are narrow, and absorption coefficients (absorption intensity) are high. Accordingly, the com-

TABLE 1

| Compounds | Chemical Formula | $\lambda_{max}$ (nm) | FWHM (nm) | Abs. coeff. ($10^4$ cm$^{-1}$) | HOMO energy level (eV) | LUMO energy level (eV) |
| --- | --- | --- | --- | --- | --- | --- |
| Synthesis Example 1 | 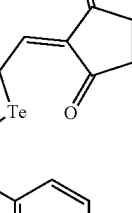 | 547 | 109 | 7.9 | −5.47 | −2.50 |
| Synthesis Example 2 | 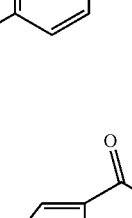 | 540 | 100 | 8.1 | −5.63 | −2.66 |
| Synthesis Example 3 | 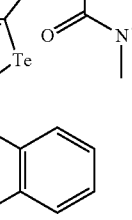 | 523 | 105 | 6.8 | −5.49 | −2.46 |
| Synthesis Example 4 | 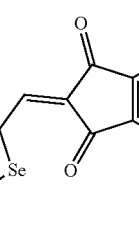 | 520 | 105 | 7.2 | −5.69 | −2.64 | pounds according to Synthesis Examples 1 to 4 exhibit improved absorption selectivity in the green wavelength region. In addition, referring to energy levels, the compounds may be appropriately used as a p-type semiconductor.

Example 1: Manufacture of Photoelectric Device

An about 150 nm-thick anode is formed by sputtering ITO on a glass substrate, and a 100 nm-thick active layer is formed thereon by codepositing a compound represented by Chemical Formula 1-1 according to Synthesis Example 1 (p-type semiconductor compound) and C60 (n-type semiconductor compound) in a volume ratio of 1:1. Subsequently, a 10 nm-thick molybdenum oxide ($MoO_x$, $0<x\leq3$) thin film is formed thereon as a charge auxiliary layer. On the molybdenum oxide thin film, a 7 nm-thick cathode is formed by sputtering ITO, manufacturing an organic photoelectric device.

Examples 2 to 4: Manufacture of Photoelectric Device

Photoelectric devices according to Examples 2 to 4 are manufactured according to the same method as Example 1 except that the compounds according to Synthesis Examples 2 to 4 are used respectively instead of the compound according to Synthesis Example 1.

Reference Examples 1 to 7: Manufacture of Photoelectric Device

Photoelectric devices according to Reference Examples 1 to 7 are manufactured according to the same method as Example 1 except that the compounds according to Reference Synthesis Example 1 to 7 are used respectively instead of the compound according to Synthesis Example 1.

Evaluation 2: Light Absorption Characteristics and EQE of Photoelectric Device

Light absorption characteristics (λmax and FWHM) in an ultraviolet (UV)-visible (UV-Vis) region of each photoelectric device according to Examples 1 to 4 and Reference Examples 1 to 7 are evaluated using Cary 5000 UV Spectroscopy (Varian Medical Systems).

In addition, external quantum efficiency (EQE) of the photoelectric devices according to Examples 1 to 4 and Reference Examples 1 to 7 is evaluated. The external quantum efficiency (EQE) is measured by using an IPCE measurement system (McScience Inc., Korea). The EQE is measured at a wavelength ranging from about 350 nm to about 750 nm by calibrating IPCE measurement system with the Si photodiode (Hamamatsu Photonics K.K., Japan) and respectively mounting the organic photoelectric devices according to Examples 1 to 4 and Reference Examples 1 to 7. In Table 2, the external quantum efficiency is measured at a maximum light absorption wavelength when a −3V voltage is applied thereto.

Of them, the results of the photoelectric devices according to Example 2 and Reference Example 2 are shown in Table 2.

Response Time Evaluation of Photoelectric Device

The photoelectric devices according to Examples 1 to 4 and Reference Examples 1 to 7 are evaluated with respect to response time (lag time). The response time is evaluated by making LED light of a peak wavelength of 530 nm enter the photoelectric devices according to Examples 1 to 4 and Reference Examples 1 to 7 from an upper electrode (a cathode) thereof, applying electric field intensity of 3 V/100 nm thereinto, and then, measuring after-image currents thereof in 0.1 second after turning off the incident LED light.

Mobility Evaluation of Photoelectric Device

Mobility of the photoelectric devices according to Examples 1 to 4 and Reference Examples 1 to 7 is evaluated. The mobility is obtained through an impedance spectroscopy analysis with reference to an article (Organic Electronics 9 (2008) 847-851). The results of the photoelectric devices of Example 2 and Reference Example 2 are shown in Table 2.

TABLE 2

| Examples | $\lambda_{max}$ (nm) | FWHM (nm) | EQE (%) at −3 V | EQE (%) at −3 V after annealing at 180° C. | Lag time @10 µW/cm² (ms) | Mobility (cm²/Vs) |
|---|---|---|---|---|---|---|
| Example 2 | 540 | 100 | 49 | 53 | 238 | 5 × 10⁻⁶ |
| Reference Example 2 | 538 | 120 | 53 | ND | 439 | 7 × 10⁻⁷ |

Referring to Table 2, the photoelectric device of Example 2 including the compound of Synthesis Example 2 exhibits a maximum absorption wavelength (λmax) at 540 nm and a low full width at half maximum (FWHM) compared with the photoelectric device of Reference Example 2 including the compound of Reference Synthesis Example 2. Accordingly, the photoelectric device of Example 2 turns out to have high wavelength selectivity in the green wavelength region. In addition, the photoelectric device of Example 2 exhibits excellent external quantum efficiency and a fast response speed and high mobility compared with the photoelectric device of Reference Example 2. In Table 2, the photoelectric device of Reference Example 2 has damages after the heat treatment at 180° C., and accordingly, EQE thereof is impossible to measure. On the contrary, the photoelectric device of Example 2 exhibits improved EQE characteristics after the heat treatment at 180° C.

While this disclosure has been described in connection with what is presently considered to be practical example embodiments, it is to be understood that inventive concepts are not limited to the disclosed embodiments. On the contrary, embodiments of inventive concepts are intended to cover various modifications and equivalent arrangements included within the spirit and scope of the appended claims.

DESCRIPTION OF SYMBOLS

| | |
|---|---|
| 10: first electrode | 20: second electrode |
| 30: active layer | 40, 45: charge auxiliary layer |
| 100, 200: photoelectric device | 300, 400, 500: organic CMOS |

-continued

| 310: semiconductor substrate | image sensor |
| 70, 72: color filter layer | 70B, 72B: blue filter |
| 60: lower insulation layer | 70R, 72R: red filter |
| 50B, 50R: photo-sensing device | 85: through-hole |
| | 80: upper insulation layer |
| | 55: charge storage |

What is claimed is:

1. A compound represented by Chemical Formula 1:

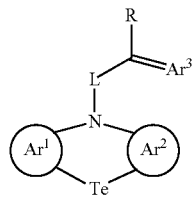

[Chemical Formula 1]

wherein, in Chemical Formula 1, $Ar^3$ is a substituted C6 to C30 hydrocarbon cyclic group, an unsubstituted C6 to C30 hydrocarbon cyclic group, or a fused ring thereof, the substituted C6 to C30 hydrocarbon cyclic group or the unsubstituted C6 to C30 hydrocarbon cyclic group of $Ar^3$ having two functional groups including one of C=O, C=S, C=Se, or C=Te, wherein carbon (C) is a ring-constituting atom, R is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, $Ar^1$ and $Ar^2$ are the same or different and are each independently a substituted or unsubstituted C6 to C30 arene group, a substituted or unsubstituted C3 to C30 heteroarene group, or a condensed ring thereof, and L is a linker represented by Chemical Formula A or Chemical Formula B,

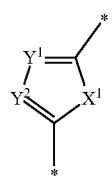

[Chemical Formula A]

wherein, in Chemical Formula A, $X^1$ is —Se—, —Te—, —O—, —S(=O)—, —S(=O)$_2$—, —NR$^a$—, —SiR$^b$R$^c$—, or —GeR$^d$R$^e$—, $Y^1$ and $Y^2$ are the same or different and are each independently CR$^f$ or N, when $Y^1$ and $Y^2$ are CR$^c$, $Y^1$ and $Y^2$ are each independently present or are linked with each other to provide a ring, R$^a$ to R$^f$ are the same or different and are each independently hydrogen, deuterium or a substituted or unsubstituted C1 to C10 alkyl group, and

* is a linking point,

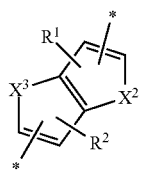

[Chemical Formula B]

wherein, in Chemical Formula B $X^2$ and $X^3$ are the same or different and are each independently —S—, —Se—, —Te—, —O—, —S(=O)—, —S(=O)$_2$—, —NR$^a$—, —SiR$^b$R$^c$—, or —GeR$^d$R$^e$—, R$^a$ to R$^e$ are the same or different and are each independently hydrogen, deuterium or a substituted or unsubstituted C1 to C10 alkyl group, and $R^1$ and $R^2$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof.

2. A compound represented by Chemical Formula 1:

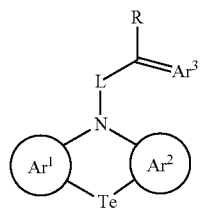

[Chemical Formula 1]

wherein, in Chemical Formula 1,

R is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, $Ar^1$ and $Ar^2$ are the same or different and are each independently a substituted or unsubstituted C6 to C30 arene group, a substituted or unsubstituted C3 to C30 heteroarene group, or a condensed ring thereof, and L is a linker represented by Chemical Formula A or Chemical Formula B,

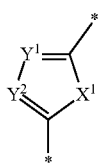

[Chemical Formula A]

wherein, in Chemical Formula A, $X^1$ is —Se—, —Te—, —O—, —S(=O)—, —S(=O)$_2$—, —NR$^a$—, —SiR$^b$R$^c$—, or —GeR$^d$R$^e$—, $Y^1$ and $Y^2$ are the same or different and are each independently $CR^f$ or N, when $Y^1$ and $Y^2$ are $CR^f$, $Y^1$ and $Y^2$ are each independently present or are linked with each other to provide a ring, $R^a$ to $R^f$ are the same or different and are each independently hydrogen, deuterium or a substituted or unsubstituted C1 to C10 alkyl group, and

* is a linking point,

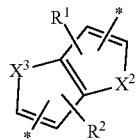

[Chemical Formula B]

wherein, in Chemical Formula B $X^2$ and $X^3$ are the same or different and are each independently —S—, —Se—, —Te—, —O—, —S(=O)—, —S(=O)$_2$—, —NR$^a$—, —SiR$^b$R$^c$—, or —GeR$^d$R$^e$—, $R^a$ to $R^e$ are the same or different and are each independently hydrogen, deuterium or a substituted or unsubstituted C1 to C10 alkyl group, and $R^1$ and $R^2$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, and $Ar^3$ is a cyclic group represented by one of Chemical Formula 2A to Chemical Formula 2F,

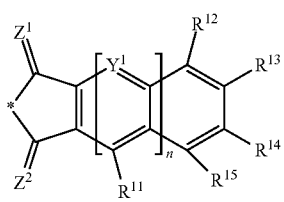

[Chemical Formula 2A]

wherein, in Chemical Formula 2A, $Z^1$ and $Z^2$ are the same or different and are each independently O, S, Se, or Te, $Y^1$ is N or $CR^a$, wherein $R^a$ is hydrogen, deuterium, or a substituted or unsubstituted C1 to C10 alkyl group, $R^{11}$, $R^{12}$, $R^{13}$, $R^{14}$, and $R^{15}$ are the same or different and are each independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof or a pair of $R^{12}$ and $R^{13}$ or a pair of $R^{14}$ and $R^{15}$ is each independently linked with each other to provide a fused aromatic ring, n is 0 or 1, and

* is a linking point,

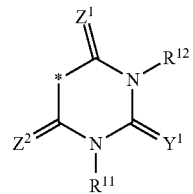

[Chemical Formula 2B]

wherein, in Chemical Formula 2B, $Z^1$ and $Z^2$ are the same or different and are each independently O, S, Se, or Te, $Y^1$ is O, S, Se, Te, or C($R^a$)(CN), wherein $R^a$ is hydrogen, a cyano group (—CN), or a C1 to C10 alkyl group, $R^{11}$ and $R^{12}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point,

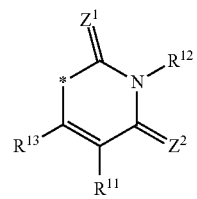

[Chemical Formula 2C]

wherein, in Chemical Formula 2C, $Z^1$ and $Z^2$ are the same or different and are each independently O, S, Se, or Te, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point,

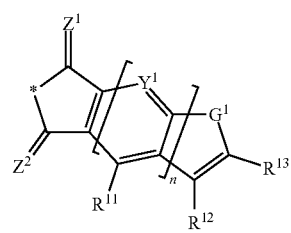

[Chemical Formula 2D]

wherein, in Chemical Formula 2D, $Z^1$ and $Z^2$ are the same or different and are each independently O, S, Se, or Te, $Y^1$ is N or $CR^a$, wherein $R^a$ is hydrogen, deuterium, or a substituted or unsubstituted C1 to C10 alkyl group, $G^1$ is —O—, —S—, —Se—, —Te—, —SiR$^x$R$^y$—, or —GeR$^z$R$^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking point,

[Chemical Formula 2E]

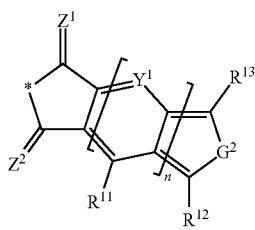

wherein, in Chemical Formula 2E, $Z^1$ and $Z^2$ are the same or different and are each independently O, S, Se, or Te, $Y^1$ is N or $CR^a$, wherein $R^a$ is hydrogen, deuterium, or a substituted or unsubstituted C1 to C10 alkyl group, $G^2$ is —O—, —S—, —Se—, —Te—, —$SiR^xR^y$—, or —$GeR^zR^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and n is 0 or 1, and

* is a linking point,

[Chemical Formula 2F]

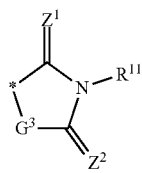

wherein, in Chemical Formula 2F, $Z^1$ and $Z^2$ are the same or different and are each independently O, S, Se, or Te, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is —O—, —S—, —Se—, —Te—, —$SiR^xR^y$—, or —$GeR^zR^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group.

3. The compound of claim 2, wherein in Chemical Formula 1, $Ar^3$ is the cyclic group represented by Chemical Formula 2B, and $Z^1$ and $Z^2$ in Chemical Formula 2B are each oxygen.

4. The compound of claim 1, wherein in Chemical Formula 1, at least one of $Ar^1$ and $Ar^2$ includes a heteroatom of nitrogen (N), sulfur (S), or selenium (Se).

5. The compound of claim 3, wherein in Chemical Formula 1, at least one of $Ar^1$ and $Ar^2$ includes a heteroatom of nitrogen (N), sulfur (S), or selenium (Se) at the position 1.

6. The compound of claim 1, wherein the N-containing heteroaromatic ring of Chemical Formula 1 is an electron donor moiety represented by Chemical Formula 4A:

[Chemical Formula 4A]

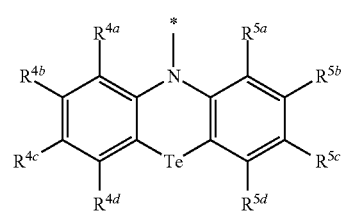

wherein, in Chemical Formula 4A, $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring.

7. The compound of claim 1, wherein the N-containing heteroaromatic ring of Chemical Formula 1 is an electron donor moiety represented by Chemical Formula 4B:

[Chemical Formula 4B]

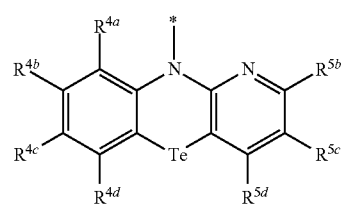

wherein, in Chemical Formula 4B, $R^{4a}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5b}$ to $R^{5d}$ are linked with each other to provide a 5-membered aromatic ring or a 6-membered aromatic ring.

8. The compound of claim 1, wherein the N-containing heteroaromatic ring of Chemical Formula 1 is an electron donor moiety represented by Chemical Formula 4C:

[Chemical Formula 4C]

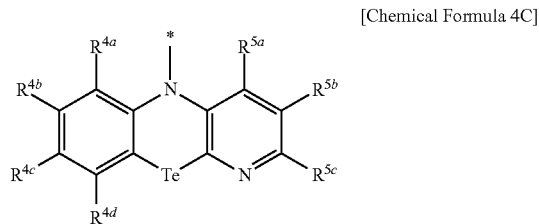

wherein, in Chemical Formula 4C, $R^{4a}$ to $R^{4d}$ and $R^{5a}$ to $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5c}$ are linked with each other to provide a 5-membered aromatic ring or a 6-membered aromatic ring.

9. The compound of claim 1, wherein the N-containing heteroaromatic ring of Chemical Formula 1 is an electron donor moiety represented by Chemical Formula 4D:

[Chemical Formula 4D]

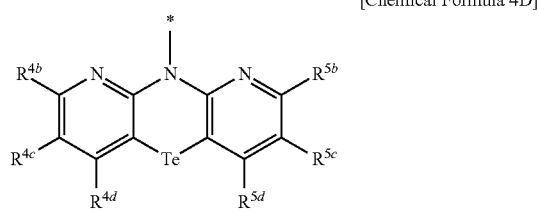

wherein, in Chemical Formula 4D, $R^{4b}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4b}$ to $R^{4d}$ are linked with each other to provide a 5-membered aromatic ring or a 6-membered aromatic ring and optionally two adjacent groups of $R^{5b}$ to $R^{5d}$ are linked with each other to provide a 5-membered aromatic ring or a 6-membered aromatic ring.

10. The compound of claim 1, wherein the N-containing heteroaromatic ring of Chemical Formula 1 is an electron donor moiety represented by Chemical Formula 4E:

[Chemical Formula 4E]

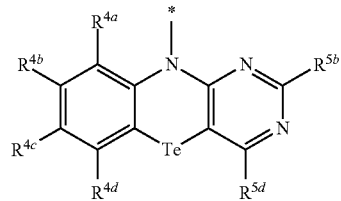

wherein, in Chemical Formula 4E, $R^{4a}$ to $R^{4d}$ and $R^{5b}$ and $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring.

11. The compound of claim 1, wherein the N-containing heteroaromatic ring of Chemical Formula 1 is an electron donor moiety represented by Chemical Formula 4F:

[Chemical Formula 4F]

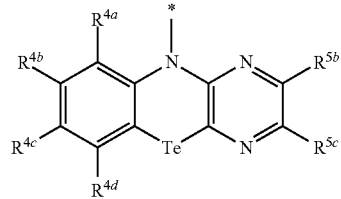

wherein, in Chemical Formula 4F, $R^{4a}$ to $R^{4d}$ and $R^{5b}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5b}$ and $R^{5c}$ are linked with each other to provide a 5-membered aromatic ring or a 6-membered aromatic ring.

12. The compound of claim 1, wherein the N-containing heteroaromatic ring of Chemical Formula 1 is an electron donor moiety represented by Chemical Formula 4G:

[Chemical Formula 4G]

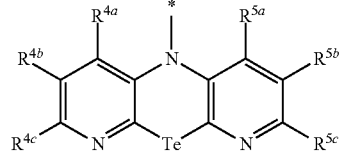

wherein, in Chemical Formula 4G, $R^{4a}$ to $R^{4c}$ and $R^{5a}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4c}$ are linked with each other to provide a 5-membered aromatic ring or a 6-membered aromatic ring and optionally two adjacent groups of $R^{5a}$ and $R^{5c}$ are linked with each other to provide a 5-membered aromatic ring or a 6-membered aromatic ring.

13. The compound of claim 1, wherein the compound has a maximum absorption wavelength ($\lambda_{max}$) in a wavelength region of greater than or equal to about 500 nm and less than or equal to about 600 nm.

14. The compound of claim 1, wherein the compound exhibits a light absorption curve having a full width at half maximum (FWHM) of about 50 nm to about 110 nm, in a thin film state.

15. The compound of claim 1, wherein a difference between a melting point of the compound and a temperature (deposition temperature) at which 10 wt % of the initial weight is lost is greater than or equal to about 3° C.

16. A photoelectric device, comprising
a first electrode and a second electrode facing each other, and
an active layer between the first electrode and the second electrode
wherein the active layer includes the compound of claim 1.

17. An image sensor comprising:
the photoelectric device of claim 16.

18. The image sensor of claim 17, wherein
the image sensor includes a semiconductor substrate integrated with a plurality of first photo-sensing devices configured to sense light in a blue wavelength region and a plurality of second photo-sensing devices configured to sense light in a red wavelength region, and
the photoelectric device is on the semiconductor substrate and is configured to selectively sense light in a green wavelength region.

19. The image sensor of claim 18, which further comprising:
a color filter layer including a blue filter configured to selectively absorb light in a blue wavelength region and a red filter configured to selectively absorb light in a red wavelength region.

20. The image sensor of claim 18, wherein the first photo-sensing device and the second photo-sensing device are stacked in a vertical direction in the semiconductor substrate.

21. The image sensor of claim 17, wherein
the photoelectric device in the image sensor is a green photoelectric device and an organic photoelectric device, and
the image sensor further includes a blue photoelectric device configured to selectively absorb light in a blue wavelength region, and a red photoelectric device configured to selectively absorb light in a red wavelength region, and
the blue photoelectric device and the red photoelectric device are stacked.

22. An electronic device comprising:
the image sensor of claim 17.

* * * * *